United States Patent [19]

Yamamoto et al.

[11] Patent Number: 5,510,106
[45] Date of Patent: Apr. 23, 1996

[54] METHODS AND COMPOSITIONS FOR VACCINATING AGAINST FELINE IMMUNODEFICIENCY VIRUS

[75] Inventors: Janet K. Yamamoto, Gainesville, Fla.; Niels D. Pedersen, Winters, Calif.

[73] Assignee: The Regents of the University of California, Oakland, Calif.

[21] Appl. No.: 335,296

[22] Filed: Nov. 7, 1994

Related U.S. Application Data

[63] Continuation of Ser. No. 995,304, Dec. 21, 1992, which is a continuation of Ser. No. 726,061, Jul. 5, 1991, abandoned, and a continuation-in-part of Ser. No. 226,447, Apr. 12, 1994, abandoned, which is a continuation of Ser. No. 823,201, Feb. 6, 1992, abandoned, which is a continuation of Ser. No. 614,474, Nov. 16, 1990, Pat. No. 5,118,602, which is a division of Ser. No. 89,700, Aug. 26, 1987, abandoned.

[51] Int. Cl.$^6$ .......................... A61K 39/00; A61K 39/38; A61K 39/21; C12N 7/00; C12N 7/01
[52] U.S. Cl. ..................... 424/207.1; 424/184.1; 424/188.1; 424/187.1; 424/208.1; 435/235.1
[58] Field of Search ......................... 424/184.1, 207.1, 424/188.1, 208.1; 435/235.1

[56] References Cited

U.S. PATENT DOCUMENTS

| | | | |
|---|---|---|---|
| 5,037,753 | 8/1991 | Pedersen et al. | 435/235.1 |
| 5,118,602 | 6/1992 | Pedersen et al. | 435/5 |
| 5,275,813 | 1/1994 | Yamamoto et al. | 424/89 |

FOREIGN PATENT DOCUMENTS

WO 90/13573  11/1990  WIPO.

OTHER PUBLICATIONS

Hohdatsu et al., 1993, Passive antibody protection of cats against feline immunodeficiency virus infection, J. Virol. 67(4):2344–2348.
Yamamoto et al., 1993, Experimental vaccine protection against homologous and heterologous strains of feline immunodeficiency virus, J. Virol. 67(1):601–605.
Talbott et al., 1989, Nucleotide sequence and genomic organization of feline immunodeficiency virus, PNAS, 86:5743–47.
Olmsted et al., 1989, Nucleotide sequence analysis of feline immunodeficiency virus: Genome organization and relationship to other lentiviruses, PNAS, 86:8088–92.
Olmsted et al., 1989, Molecular cloning of feline immunodeficiency virus, PNAS, 86:2448–52.
Jarrett, O. et al. (1990) AIDS 4 (Suppl. 1):S163–165.
Berzofsky, J. A. et al. (1991), J. AIDS 4:451–459.
Pedersen et al. (1987) Science 235:790–793.
American Assoc. for Can. Res., May 23, 1987, Ab. No. 3337.
the 3rd Int'l. Conf. on AIDS. Jun. 1–5, 1987.
Yamamoto et al. Fed. Amer. Soc for Experimental Biology, Apr. 2, 1987.
Yamamoto et al. (1988) Leukemia, Dec. Supp. 2:204S–215S.
Yamamoto et al. (1988) Am J. Vet. Res. 49:1246–1258.
Ackley et al. (1990) J. Virol. 64:5652–5655.
Olmstead et al. (1989) PNAS USA 86:2448–2452.
Hosie and Jarrett (1990) AIDS 4:215–220.
Stott et al. (1990) Lancet 336:1538–1541.
Desrosiers et al. (1989) PNAS USA 86:6353–6357.
Murphey–Corb et al. (1989) Science 246:1293–1297.
Carlson et al. (1990) AIDS Res. Human Retrovir. 6:1239–1246.
Berman et al. (1990) Nature 345:622–625.
Stephens et al. 1992, Analysis of the Amino Acid Terminal Presequence of the Feline . . . Virology 190:569–578.

*Primary Examiner*—James C. Housel
*Assistant Examiner*—N. M. Minnifield
*Attorney, Agent, or Firm*—Townsend and Townsend and Crew

[57] ABSTRACT

Compositions derived from a novel viral isolate designated feline immunodeficiency virus (FIV) include the whole virus, proteins, polypeptides and, polynucleotide sequences derived from the virus; and antibodies to antigenic sites on the virus. These compositions are useful in a variety of techniques for the detection of and vaccination against FIV. Detection methods disclosed include immunoassays for both the virus and antibodies to the virus, and the use of polynucleotide probes to detect the viral genome. Vaccines include both wholly and partially inactivated viruses inactivated cell lines expressing FIV antigens, and subunit vaccines. Whole, live virus is also useful as a model system for predicting the behavior of human immunodeficiency virus (HIV).

3 Claims, 13 Drawing Sheets

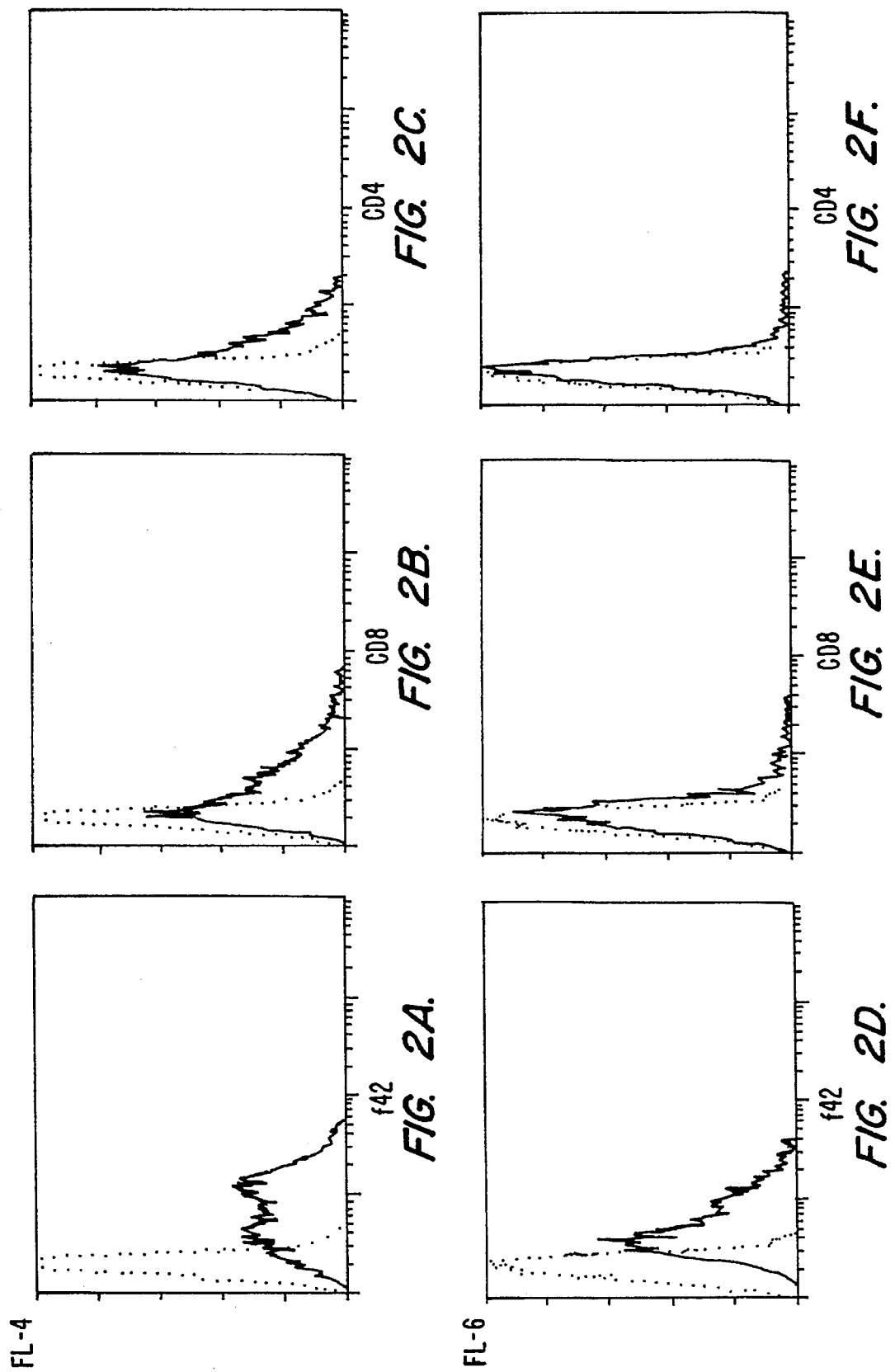

METHODS AND COMPOSITIONS FOR VACCINATING AGAINST FELINE IMMUNODEFICIENCY VIRUS

This application is a continuation application Ser. No. 07/995,304, filed on Dec. 21, 1992, which was a continuation of application Ser. No. 07/726,061, filed on Jul. 5, 1991, now abandoned. This application is also a continuation-in-part of application Ser. No. 08/226,447, filed on Apr. 12, 1994, which was a continuation of application Ser. No. 07/832,201, filed on Feb. 6, 1992, now abandoned, which was a continuation of application Ser. No. 07/614,474, filed on Nov. 16, 1990, now U.S. Pat. No. 5,118,602, which was a division of application Ser. No. 07/089,700, filed on Aug. 26, 1987, now abandoned.

BACKGROUND OF THE INVENTION

1. Field of the Invention

The present invention relates generally to the detection and treatment of vital infection. More particularly, the invention relates to compositions and methods useful for the diagnosis of and vaccination against infection with a newly-discovered lymphotropic retrovirus, initially designated as feline T-lymphotropic lentivirus and presently designated feline immunodeficiency virus (FIV).

Domestic cats may become infected with several retroviruses, including feline leukemia virus (FeLV), feline sarcoma virus (FeSV), endogenous type C oncornavirus (RD-114), and feline syncytia-forming virus (FeSFV). Of these, FeLV is the most significant pathogen, causing diverse symptoms, including lymphoreticular and myeloid neoplasms, anemias, immunemediated disorders, and an immunodeficiency syndrome which is similar to human acquired immune deficiency syndrome (AIDS). Recently, a particular replication-defective FeLV mutant, designated FeLV-AIDS, has been more particularly associated with immunosuppressive properties.

While immunodeficiency syndrome in cats has normally been associated with FeLV, immunodeficiency-like symptoms have been observed in cats which are seronegative for FeLV, usually without alternative explanation. It would be desirable to identify etiological agents other than FeLV which are responsible for causing immunodeficiency in cats. It would be particularly desirable to provide methods and compositions for the detection of and vaccination against such newly-identified etiological agents, and in particular, against FIV.

2. Description of the Background Art

The discovery of feline T-lymphotropic lentivirus (now designated feline immunodeficiency virus) was first reported in Pedersen et al. (1987) Science 235:790–793. Abstracts concerning the discovery of the virus have been presented at the American Association for Cancer Research on May 23, 1987 (Abstract No. 3337); and The Third International Conference on Acquired Immune Deficiency Syndrome, June 1–5, 1987. A poster concerning discovery of the virus was presented at a meeting of the Federation of American Society for Experimental Biology on Apr. 2, 1987.

Characteristics of FIV have been reported in Yamamoto et al. (1988) Leukemia, December Supplement 2:204S–215S; Yamamoto et al. (1988) Am. J. Vet. Res. 49:1246–1258; and Ackley et al. (1990) J. Virol. 64:5652–5655. Cloning and sequence analysis of FIV have been reported in Olmsted et al. (1989) Proc. Natl. Acad. Sci. USA 86:2448–2452 and 86:4355–4360; and Talbott et al. (1989) Proc. Natl. Acad. Sci. USA 86:5743–5747. Hosie and Jarret (1990) AIDS 4:215–220, describes the serological response of cats infected with FIV.

A portion of the experimental data presented in this application was published in AIDS 1990 4 (Suppl. 1):S163–S165.

Inactivated cell-virus and cell-free whole simian immunodeficiency vaccines have been reported to afford protection in macaques (Stott et al. (1990) Lancet 36:1538–1541; Desrosiers et al. PNAS USA (1989) 86:6353–6357; Murphey-Corb et al. (1989) Science 246:1293–1297; and Carlson et al. (1990) AIDS Res. Human Retroviruses 6:1239–1246). A recombinant HIV gp120 vaccine has been reported to afford protection in chimpanzees (Berman et al. (1990) Nature 345:622–625).

SUMMARY OF THE INVENTION

Compositions and methods are provided for vaccination against a novel feline retrovirus designated feline immunodeficiency virus (FIV), previously designated feline T-lymphotropic lentivirus (FTLV). The compositions include vaccines comprising an immunogen capable of eliciting an immune response protective against infection by FIV when administered in an effective amount to a susceptible host. The immunogen will display determinant sites characteristic of the virus, such as those found on the major envelope and core proteins. The preferred immunogens include inactivated whole virus, attenuated whole virus, and inactivated cell lines infected with FIV and which express FIV antigens on their surface. Other immunogens which may find use include polypeptides which mimic the determinant sites, such as FIV peptides (to produce subunit vaccines), anti-idiotype antibodies, and the like.

According to the method of the present invention, the vaccine compositions are administered to susceptible hosts, usually cats, in amounts effective to afford immunity against subsequent challenge by FIV. The vaccines may be administered by any conventional route, including subcutaneously, intramuscularly, and oranasally, and will usually be administered at least twice over intervals spaced-apart by one or more weeks to achieve the desired immunity.

Figure 1:
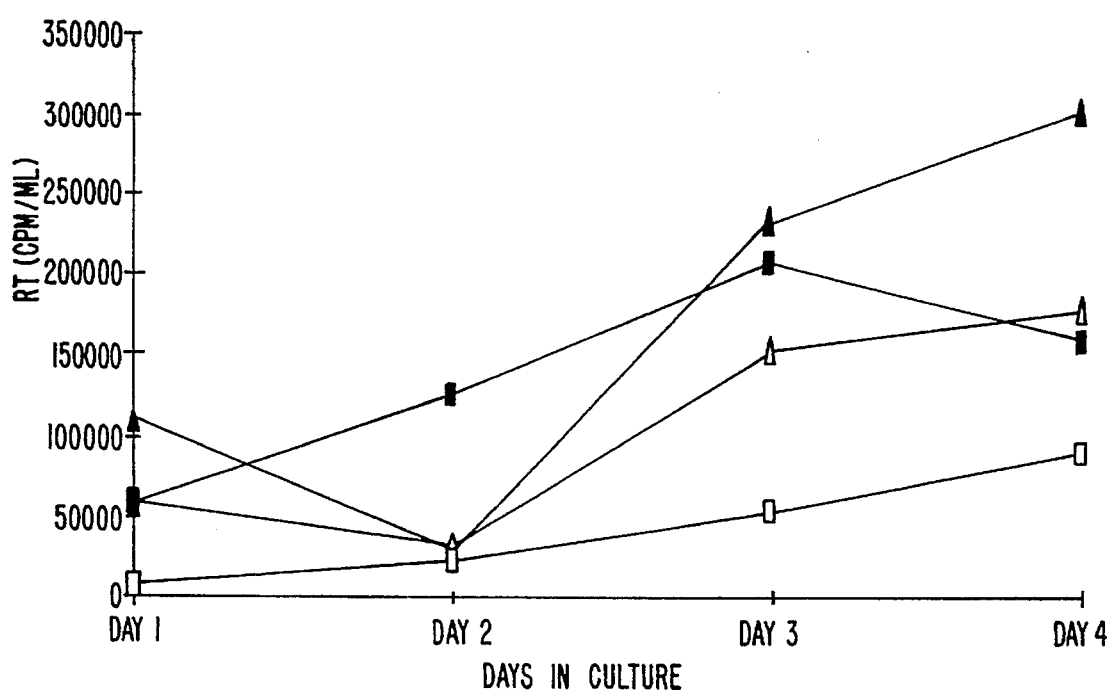
FIG. 1
Figure 3A:
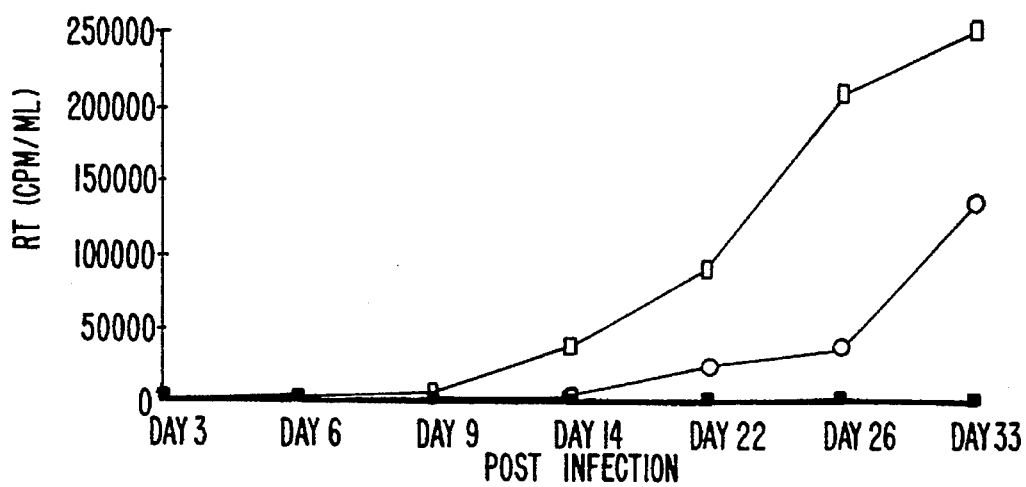
Figure 3B:
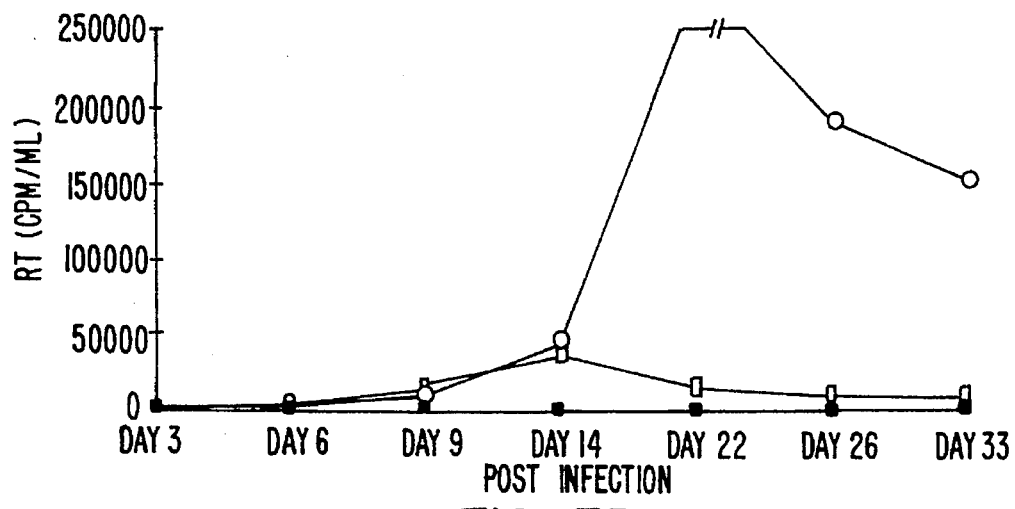
Figure 3C:
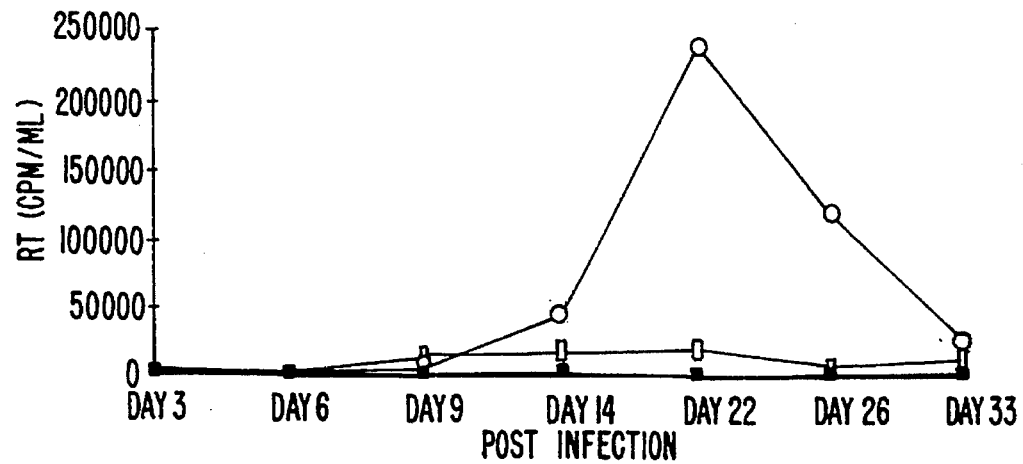
Figure 3D:
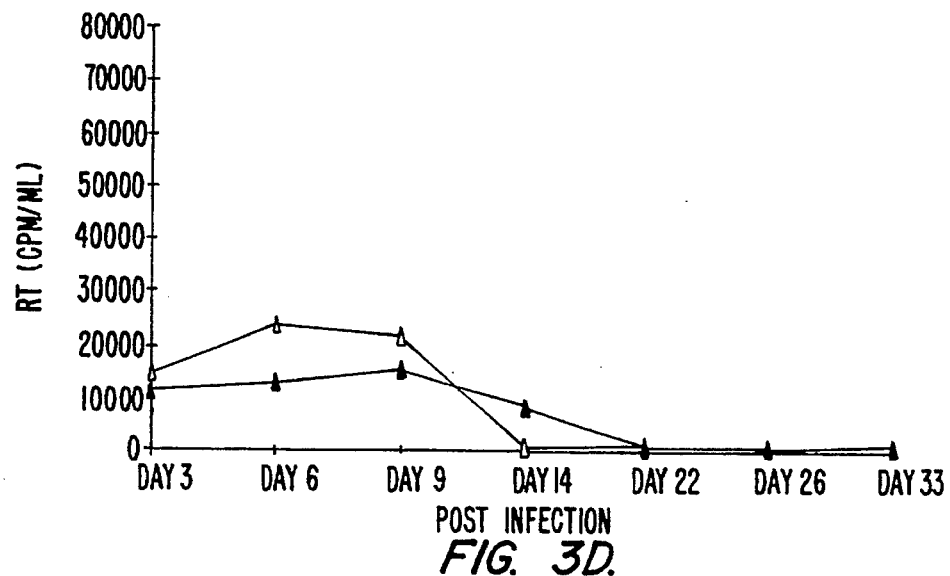
Figure 3E:
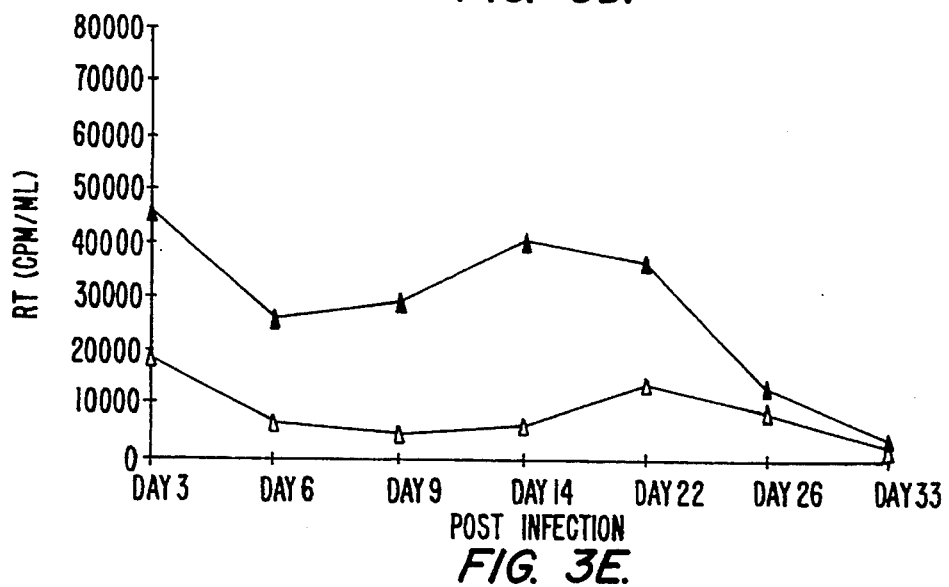
Figure 3F:
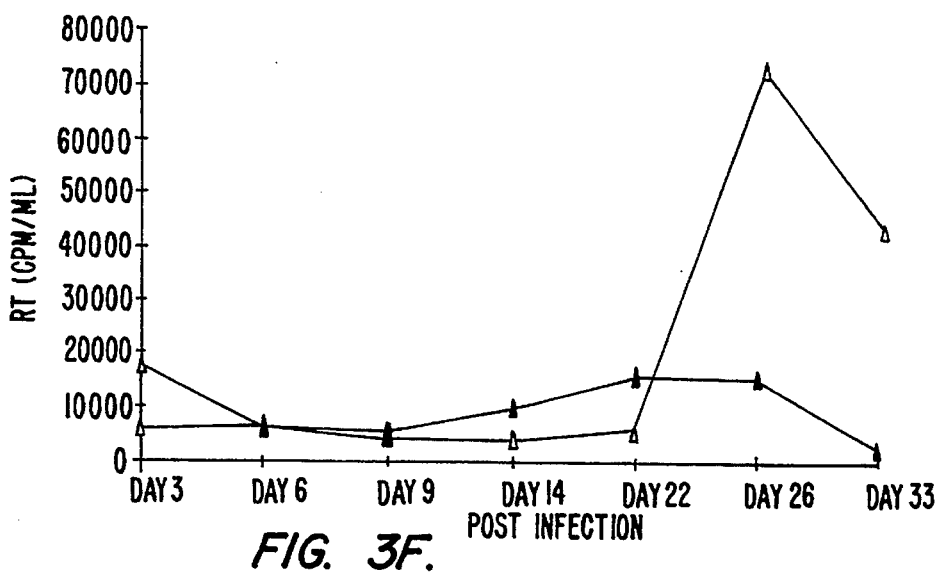

FL-4 (▲), FL-6 (△), FIV-FeT1 (■), and FIV-CRFK (□) cells were seeded at $5 \times 10^5$ cells/ml and tested daily for the RT activity in their culture fluids. A gradual increase in RT activity was observed over the four days of culture, with peak RT titers detected on Day 4 for all cell cultures except FIV-FeT1 which had it on Day 3. Peak viable cell counts ($1.0–2.25 \times 10^6$ cells/ml) were observed on Day 3 for all cell cultures except for the FIV-FeT1 culture which had its peak viable cell count ($1.3 \times 10^6$ cells/ml) on Day 2. The percent cell viabilities during the four days of culturing were 75–90% for FIV-FL-4, 70–90% for FIV-FL-6, 70–80% for FIV-CRFK, and 55–65% for FIV-FeT1.

FIGS. 2A–2F

The FACS profiles of the surface phenotype of FL-4 (FIGS. 2A, 2B, and 2C) and FL-6 (FIGS. 2D, 2E, and 2F) were determined using characterized monoclonal antibodies to feline CD4 (Fel 7), CD8 (FT2), pan T-cell (F42), and the feline light chain and μ heavy chain specific (AC5) markers. Both cell lines had cell populations which were positive for CD4 (FIGS. 2C, and 2F), CD8 (FIGS. 2B and 2E), and pan T-cell (FIGS. 2A and 2D). Both FL-4 and FL-6 cells tested negative by FACS analysis for surface B cell markers using monoclonal antibodies (AC5) (data not shown). The solid lines represent the FACS profiles of FL-4 and FL-6 cells and the dotted lines represent the FACS profiles of negative control cells. The percentages of FL-4 cells that were positive for CD4, CD8 and pan T-cell markers were 10%, 20%, and 80% respectively. The percentages of FL-6 cells that were positive for CD4, CD8 and pan T-cell markers were <8%, 11%, and 76%, respectively. Depending on the culture conditions, expression of CD4 and CD8 on the cell membrane can be decreased or eliminated. The abscissa represents fluorescence intensity and the ordinate represents relative cell number.

FIGS. 3A–3F

FIV from FL-4 (A,D), FIV-FeT1 (B,E) and FIV-CRFK (C,F) cells were tested for their infectivity on different feline PBLs (A,B,C) and feline thymocytes (D,E,F). Uninfected feline lymphoid cells used in this study were FeT1.1 (■), FeT1.2 (□), FeT1.3 (o), Thy1 (△), and Thy2 (▲). All of the FeT1 cells were derived from uninfected PBLs and Thy cells were primary thymocytes obtained from FIV-free kittens. FeT1.1, FeT1.2, and FeT1.3 were subclones of the uninfected FeT1 line, which was the precursor line for FIV-FeT1 cells. The percentage of cells that was positive for CD4 and CD8 markers was <2% and 5% for FeT1.1, <2% and <2% for FeT1.2, and <2% and 4% for FeT1.3, 54% and 4% for Thy 1, and 38% and <2% for Thy2, respectively. Interestingly, FIV from all cell lines were able to either transiently and persistently infect all lymphoid cells except for those from FeT1.2 cultures, whose cells also totally lacked the expression of both CD4 and CD8 markers. Another observation was that FIV from FL-4 and FIV-FeT1 cells infected thymocytes more rapidly but produced a lower titer of virus than those produced by FeT1.1 or FeT1.3 cells. The major difference between the thymocytes and the FeT1.1 or FeT1.3 cells was the large number of $CD4^+$ cells present in the thymocyte cultures. Thus, this observation suggests that the rapid FIV infection of the thymocytes was correlated to the increased number of $CD4^+$ cells.

FIG. 4

Immunoblot analysis was performed on the sera from cats inoculated with 2 ml of cell-free TCF (150,000 cpm/ml RT activity) from either FL-4 (Cat #172) or FL-6 (Cat #177) cultures. The FIV antibody development in these cats was similar to the progression observed previously in SPF cats inoculated with plasma or blood from FIV-infected cats or with TCF from primary PBL cultures (Yamamoto et al., (1988) supra.). Their immunoblot profiles at 16 weeks post-inoculation (pi) resembled those of sera from naturally (Cat #C9) or experimentally (Cat #H6) infected cats. The PBLs from these cats at 10 weeks pi were positive for FIV by virus isolation (data not shown). Both immunoblot and virus isolation results demonstrate that these cats were infected with FIV.

Figure 5A:
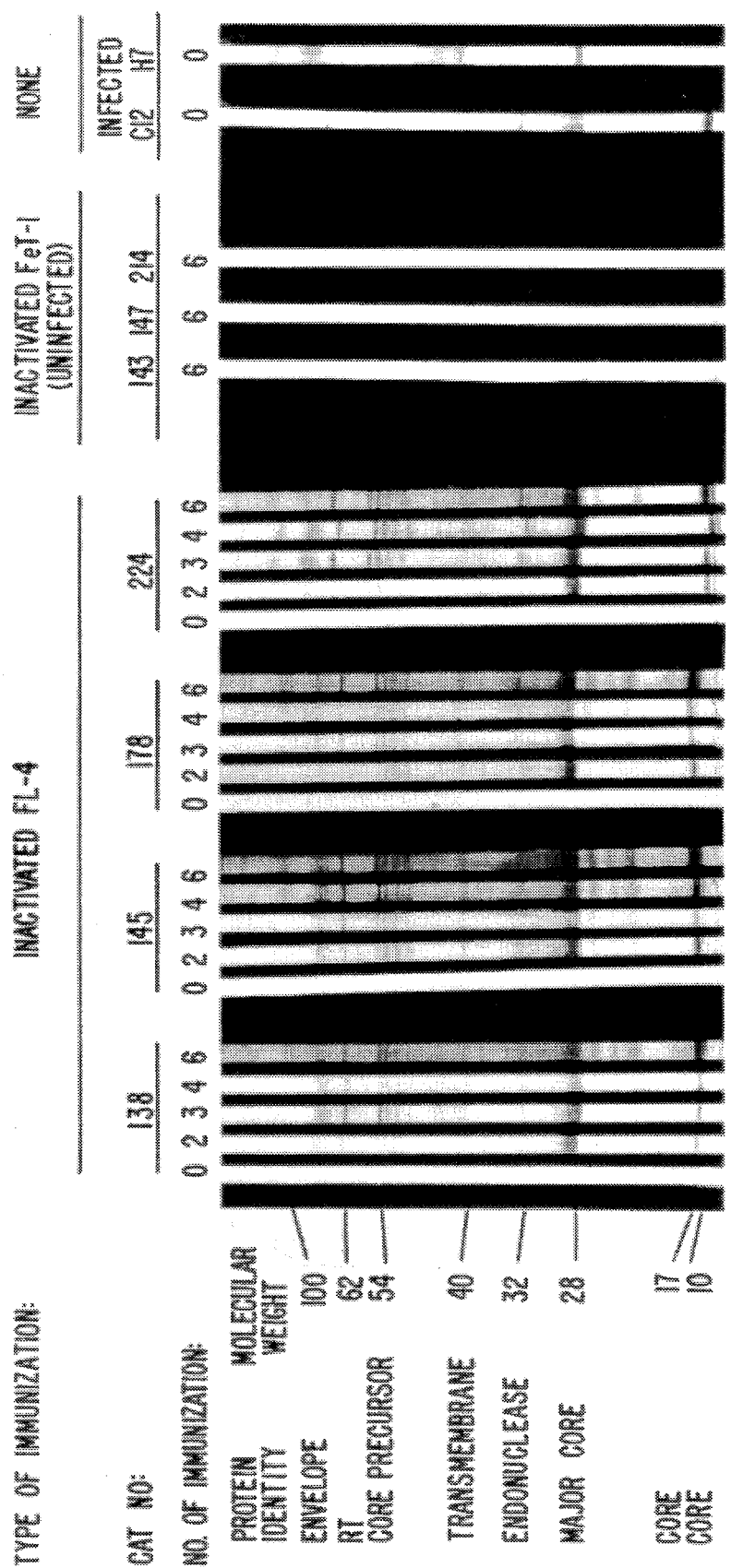
Figure 5B:
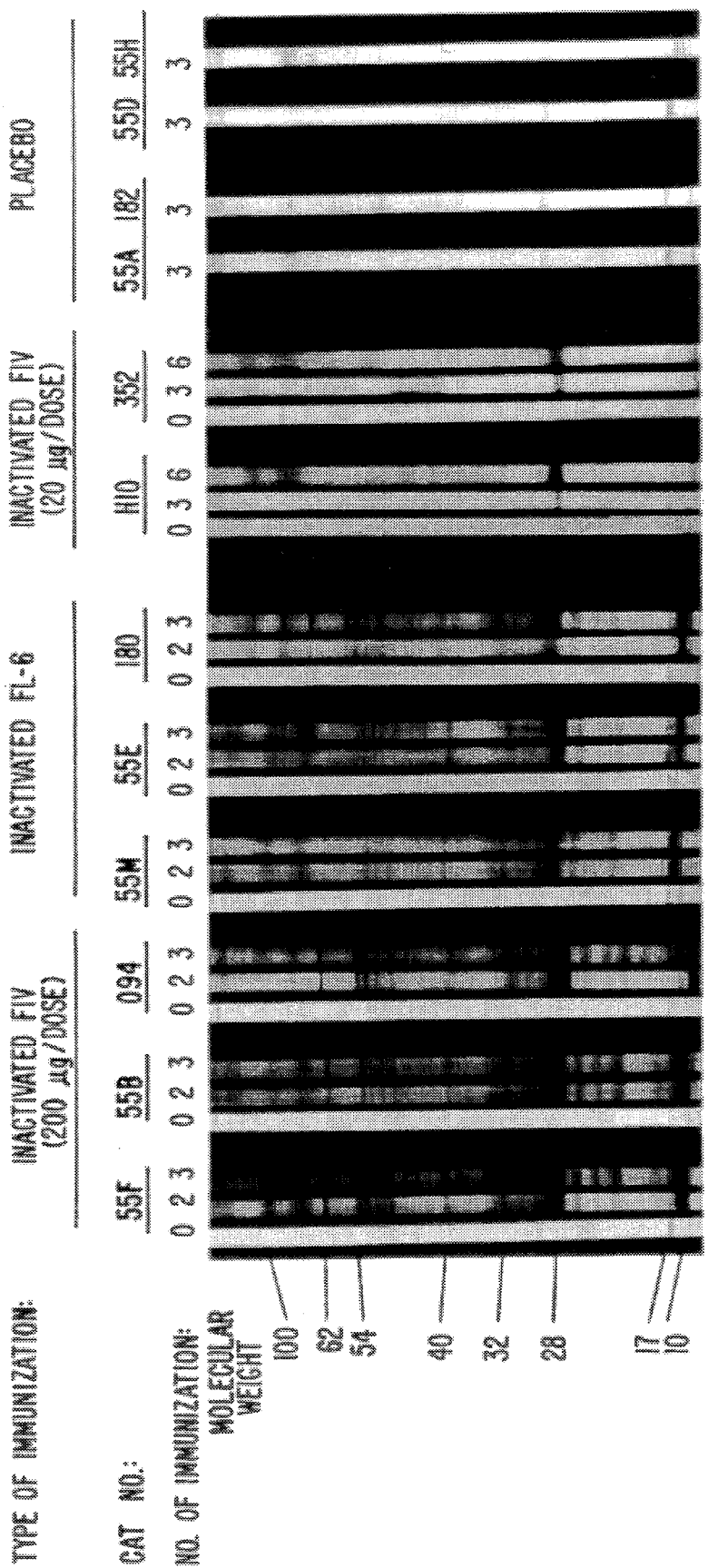

FIGS. 5A and 5B

The immunogenicity of the FIV produced from our FIV-infected cell lines was evaluated in cats. The reactivities of the antibodies produced in cats immunized with either inactivated FL-4 (A) or FL-6 (B) cells or with inactivated FL-4-produced virus (B) were determined by immunoblot analysis. Cats were immunized six-times with inactivated FL-4 or uninfected FeT1 cells and their serum immunoblot profiles were compared to those of serum from cats naturally (Cat #C12) or experimentally (Cat #H7) infected with FIV (A). Cats were also immunized four-times with inactivated FIV (produced by FL-4 cells) and with inactivated FL-6 cells (B) and evaluated similarly. In the last study, cats were immunized eight-times with 20 μg per dose of inactivated FIV and these results presented. All immunizations were done at two week intervals except for the final interval between the fifth and sixth immunizations in the first study. The adjuvants used were either MDP (A) or a combination of Freund's complete and incomplete adjuvants (B). The predicted molecular masses of the FIV proteins, derived from nucleotide sequence analysis (Olmstead et al. (1989) supra., and Talbott et al. (1989) PNAS USA 86:5743–5747), have been identified as: 24.5–25.1 kD for major core protein, 14.7–14.9 kD for N-terminal gag protein (minor core protein), 9.5–9.6 kD for nucleocapsid protein (minor core protein), 49.2–49.5 kD for gag precursor protein (core precursor), 61.5 kD for reverse transcriptase (RT), 30.7 kD for endonuclease, 100 kD for major envelope glycoprotein (outer membrane), 36 kD for transmembrane glycoprotein, and 140 kD for precursor envelope glycoprotein. The banding profiles derived from radioimmunoprecipitation analysis using $[^3H]$glucosamine (Olmstead et al. (1989) PNAS USA 86:4355–4360 and Hosie et al. (1990) AIDS 4:215–220) or $[^{35}S]$methionine/$[^{35}S]$cysteine (O'Connor et al. (1989) J. Clin. Micro. 27:474–479), have demonstrated a gp100–120 band for envelope, a gp36–41 diffuse band for transmembrane, and a gp130–140 band for envelope precursor. The molecular weights of the viral protein components, as described by the above analyses, correspond to the immunoblot patterns of 24–28 kD for major core, 15–kD for minor core, 10 kD for minor core, 54–55 kD for core precursor, 62 kD for RT, 32 kD for endonuclease, 37–44 kD (diffuse band) for transmembrane, and 100–120 kD for envelope (Yamamoto et al. (1988) supra.; Hosie et al. (1990) supra.; and O'Connor et al. (1989) J. Clin. Micro. 27:474–479). In this study, the development of antibodies to major core protein p28 was observed prior to the development of antibodies to the envelope glycoprotein gp100 in both immunization studies (A and B). Our immunoblot analysis of the sera from immunized cats closely resembled the immunoblot profiles of FIV-infected cats previously published by our laboratories and others (Yamamoto et al. (1988) supra.; Hosie et al. (1990) supra.; and O'Connor et al. (1989) J. Clin. Micro. 27:474–479). Comparison of high dose (200 μg) indicates that large amounts of viral proteins are required to adequately and rapidly induce FIV antibodies (B). The immunoblot numbers represent the cat identification numbers.

Figure 6A:
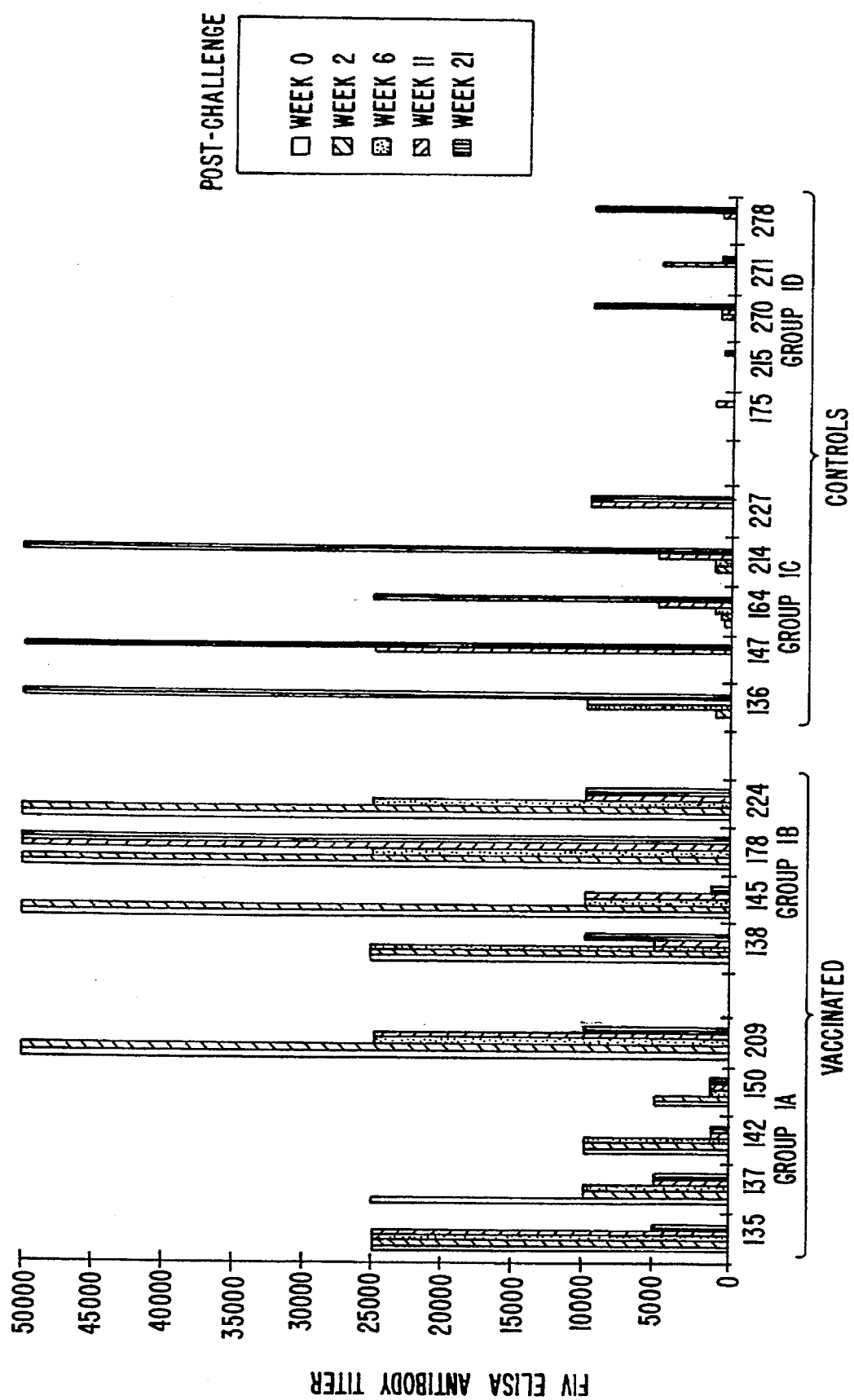
Figure 6B:
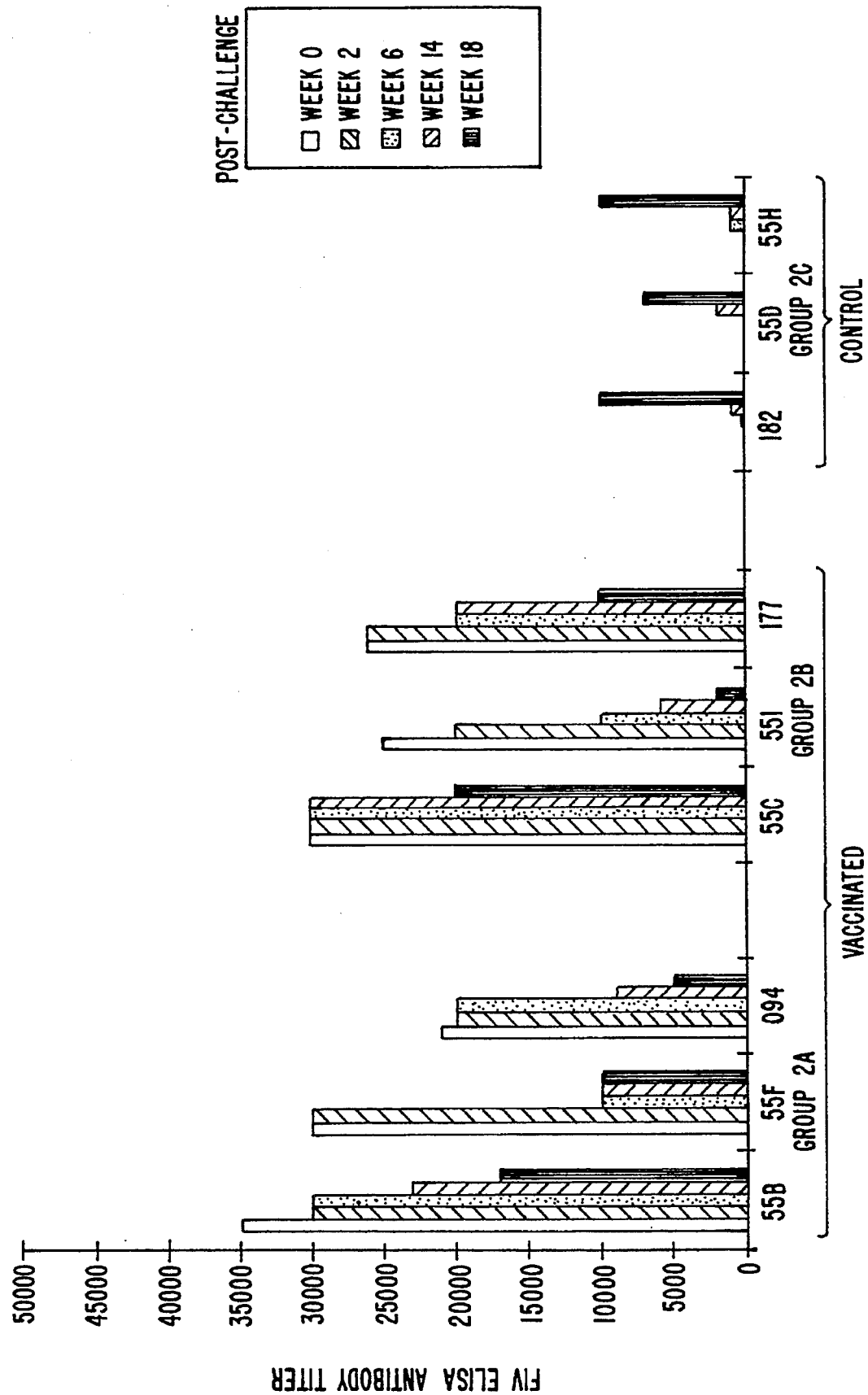

FIGS. 6A and 6B

The FIV IgG antibody titer was measured by enzyme-linked immunosorbent assay (ELISA) using 250 ng/microwell of sucrose-gradient purified FIV as substrate and biotinylated goat anti-cat IgG (Vector Laboratories, BA-9000) as conjugating antibody (Pedersen et al. (1987) Science 235:790–793). Sera from the different bleeding dates of each cat were serially diluted and assayed simultaneously in a single test. The results are based on two separate ELISA testings. Part A gives the results from cats immunized with the fixed cell-virus vaccine and part B gives results from cats immunized with the inactivated whole-virus vaccine.

FIG. 7

Immunoblot analysis was performed on sera at a final dilution of 1:50 from cats immunized with fixed cell-virus or inactivated whole-virus vaccines. Results presented are those from cats immunized with fixed FIV-FL-4 cells (Group 1B), inactivated FIV (Group 2A), or fixed uninfected FeT1 cells (Group 1C). Lane A is an immunoblot profile of a SPF cat experimentally infected with FIV.

Figure 8A:
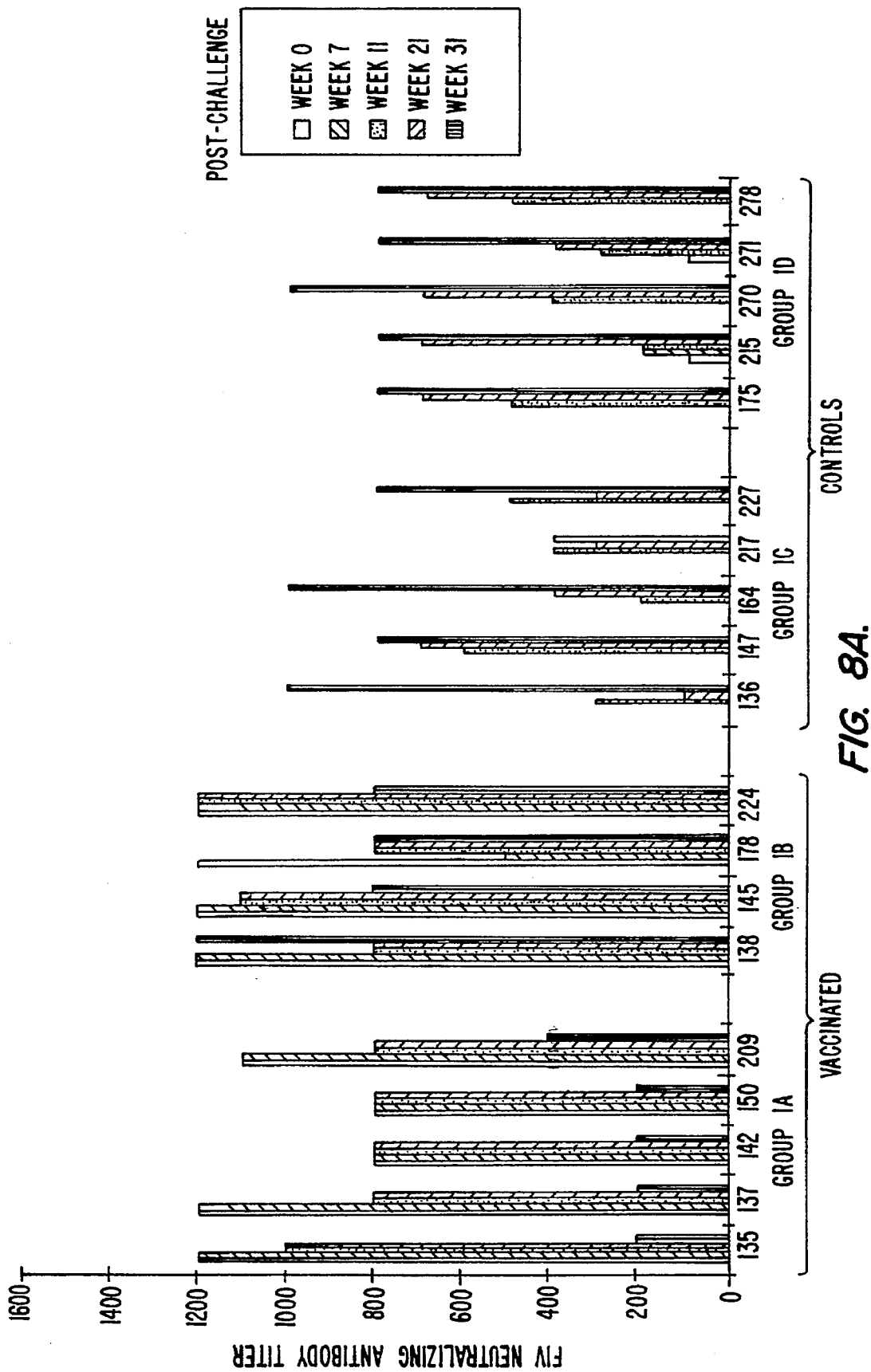
Figure 8B:
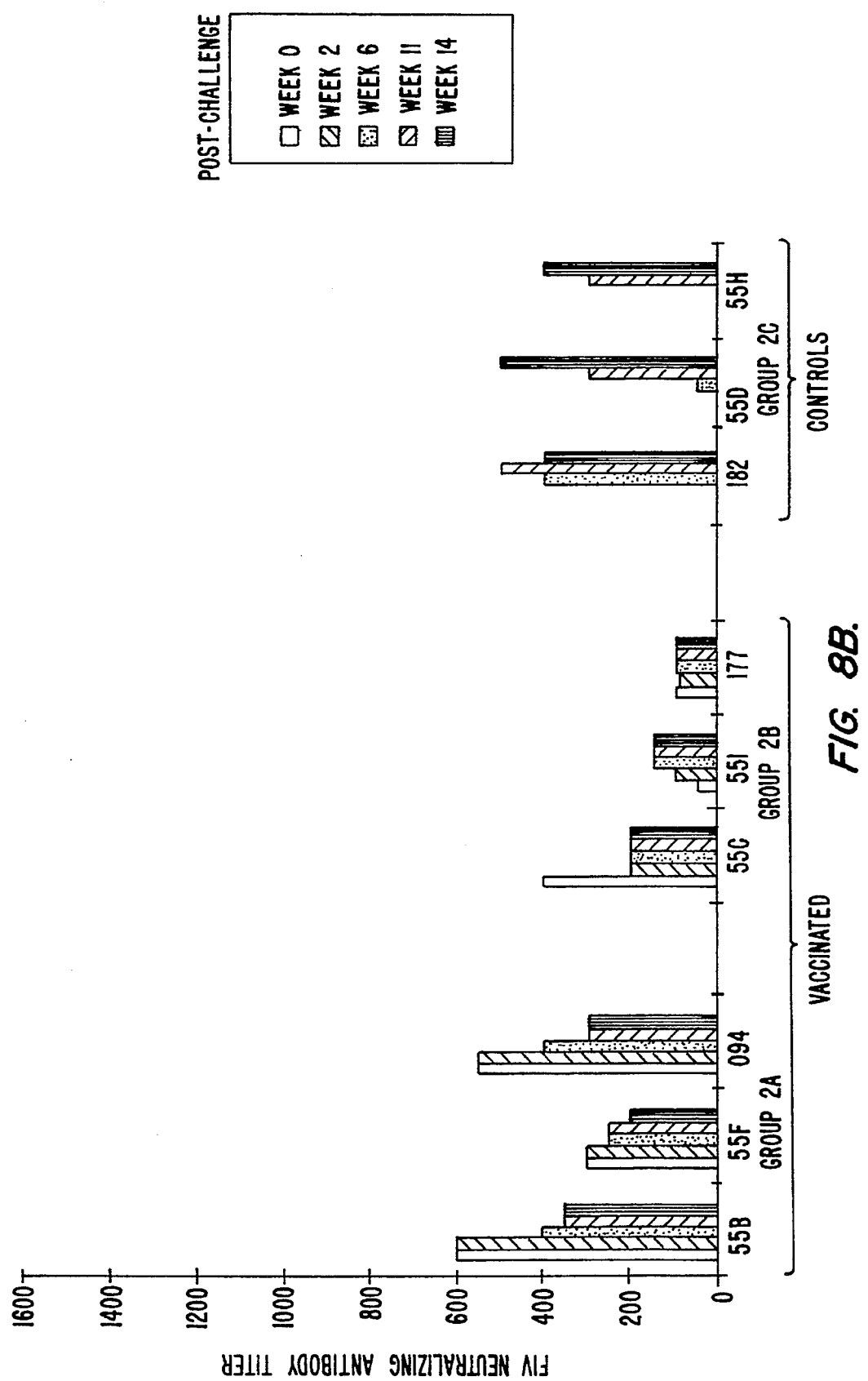

FIGS. 8A and 8B

The neutralizing antibody titers to FIV were assayed the FIV-susceptible feline lymphoid cell line FeT1. In brief, diluted samples of heat-inactivated serum (56° C. for 30 min) were incubated with 100 tissue culture infective doses (TCID$_{50}$) of FIV (Petaluma strain) for 45 min at 37° C. in a 25-cm flask. The FeT1 cells were added to this mixture at a final concentration of $2 \times 10^5$ cells/ml. After three days of culturing, the cells were washed once with Hank's balanced salt solution to remove residual virus from the culture and then resuspended in fresh culture media (RPMI 1640 containing 10% heat-inactivated fetal calf serum, 10 mM HEPES buffer, 50 µg/ml gentamicin, $1 \times 10^5$ M 2-mercaptoethanol, and 100 U/ml human recombinant IL-2). Virus infection was monitored by $Mg^{++}$-dependent RT assays of the culture fluid. The serum was considered positive for neutralizing antibodies when RT activity was $\leq 50\%$ of the infected control culture which had no serum exposure. Nonspecific antiviral activity (i.e., interferon activity) was not detected in the heat-inactivated serum samples using the antiviral assay with vesicular stomatitis virus (Yamamoto et al. (1986) Vet. Immunol. Immunopathol. 11:1–19). Part A gives the results from cats immunized with the fixed cell-virus vaccine and part B gives results from cats immunized with the inactivated whole-virus vaccine.

Figure 9A:
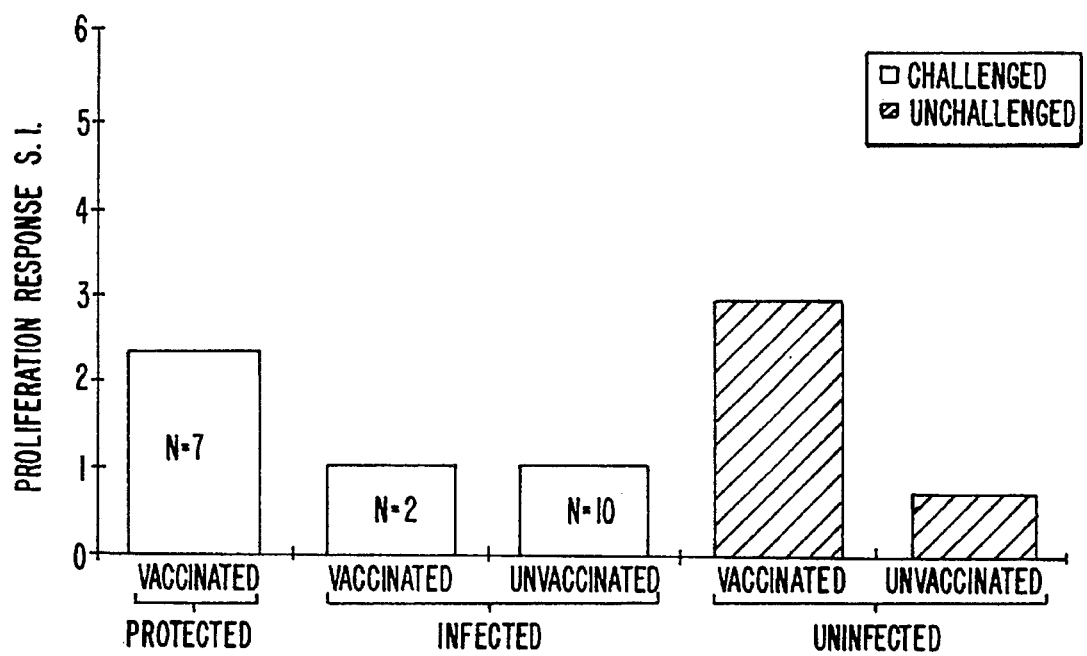
Figure 9B:
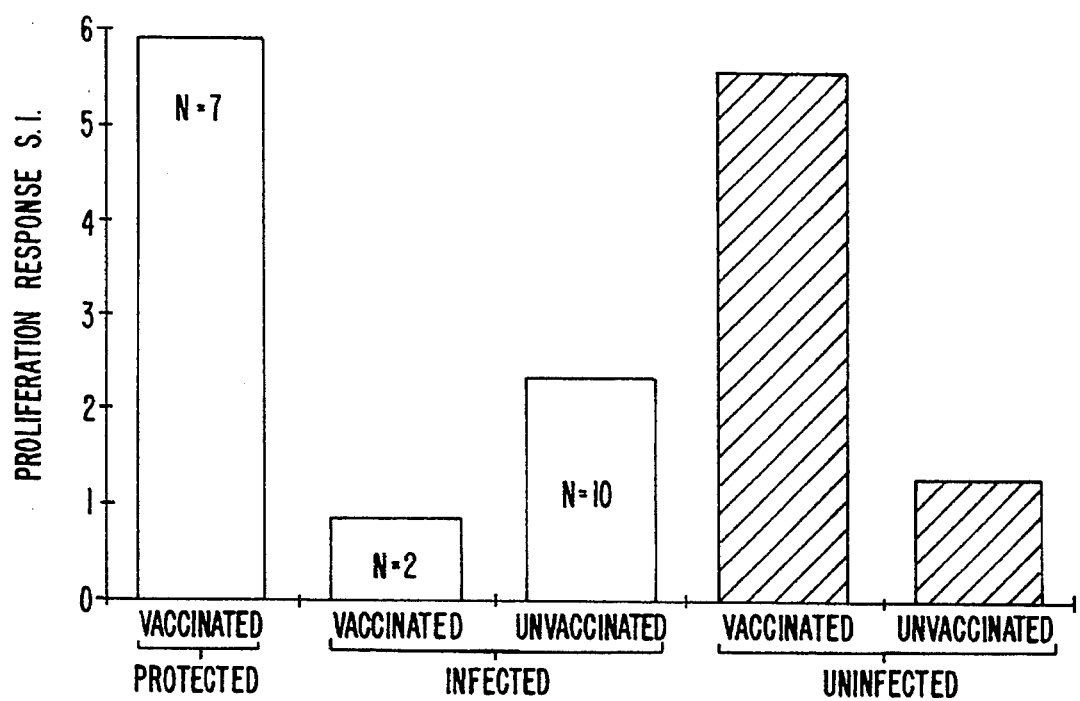

FIGS. 9A and 9B

Cellular immunity of the cats immunized with the fixed cell-virus vaccine was monitored by assaying the PBLs for their ability to proliferate (FIG. 9A) or produce IL-2 (FIG. 9B) upon stimulation with inactivated whole FIV (1.25% paraformaldehyde inactivated). The PBLs were isolated from blood harvested at 27 weeks pc from all challenged animals and at 14 weeks post-immunization from unchallenged cats. The proliferation assay consisted of $^3$H-thymidine incorporation by PBLs ($1 \times 10^5$ cells/microwell) upon stimulation with inactivated FIV (4.5 µm/microwell) for five days at 37° C. Similarly, 1.5 ml-cultures of PBL ($1 \times 10^6$ cells/ml) were incubated with FIV antigens (50 µm/ml) for two days and the culture fluid was assayed for IL-2 titer. The IL-2 assay consisted of measuring the amount of $^3$H-thymidine incorporation of the IL-2-dependent murine HT-2C cells in presence or absence of IL-2 containing samples (Gillis et al. (1978) J. Immunol. 120:2027–2032). When compared to infected, unvaccinated control cats, the vaccine protected cats and the vaccinated but unchallenged cats responded significantly (stimulation index $\geq 2.0$) to FIV antigenic stimulation in both proliferation ($P<0.001$) and IL-2 induction ($P<0.001$) assays. The P value was derived by using two-tailed t-test. Part A presents the results from the proliferation assay and part B the results from the IL-2 induction assay.

DESCRIPTION OF THE SPECIFIC EMBODIMENTS

A novel virus designated feline immunodeficiency virus (FIV), previously designated feline T-lymphotropic lentivirus (FTLV) has been discovered and isolated in substantially pure form. The virus is infectious in cats, causing a wide variety of symptoms, including abortion, alopecia, anemia, chronic rhinitis, conjunctivitis, diarrhea, emaciation, enteritis, gingivitis, hematochezia, neurologic abnormalities, periodontitis, and seborrheic dermititis. The course of the disease is usually fatal.

The etiology, pathogenssis, and morphology of FIV closely resemble those of human immunodeficiency virus (HIV) and simian T-lymphotropic virus III (SAIDS), which cause acquired immunodeficiency syndrome in humans and primates, respectively. FIV does not appear to be antigenically related to HIV or to SAIDS, but rather appears to be a species-adapted lentivirus that has existed in cats for some time. Preliminary surveys conducted by the inventors herein indicate that FIV infection in cats may be widespread, possibly accounting for a significant proportion of the immunodeficiency symptoms found in cats who are free from FIV infection.

FIV is a feline immunodeficiency virus characterized as a retrovirus, more specifically as a lentivirus, which is tropic for T-lymphocytes of the host which it infects. The virus is also characterized by horizontal transmission, and may further be characterized by vertical transmission in at least some cases.

It is expected that FIV is polymorphic, and reference to FIV in the present application is intended to encompass the entire FIV family, including a variety of strains which share substantial amino acid sequence and nucleotide sequence homology and which are immunologically related. Substantial amino acid sequence homology means at least about 75% homology, usually at least about 80% homology, and frequently 90% homology and above in at least some of the viral genes and proteins. For example, the env, gag, or pol regions may display the requisite homology, while the genome as a whole does not. In such cases, so long as the viruses are immunologically related, the viruses will be considered to be FIV within the ambit of the present invention.

By immunologically related it is meant that the various strains will display substantial serologic cross-reactivity with the newly-discovered strain which has been deposited. Serologic cross-reactivity is defined as the ability of an antiserum or antibodies specific for the deposited FIV strain to react with other FIV strains as well as the deposited strain. Usually, immunologically related strains will cross-react with antibodies specific for more than one epitopic site, usually more than five epitopic sites, and frequently ten or more epitopic sites.

Conveniently, FIV strains may be identified by Western blot analysis where purified virus is disrupted with a suitable detergent, e.g., sodium dodecyl sulfate, and separated on a slab gel by electrophoresis. The separated polypeptide bands are transferred from the gel to nitrocellulose filter paper and visualized with labelled antibody. The molecular weights of the various resolved bands may then be determined by comparison to known molecular weight standards. Substantial similarity between the Western blot analysis of an unidentified virus and that of a known FIV virus indicates that the unknown virus is likely an FIV virus.

Other FIV isolates have been characterized, indicating that the nucleotide sequence of the envelope gene varies by no more than about 15% among isolates. Such isolates, from different regions, are described in Masashi et al. (1990) In: Proc. 6th Intnl. Conf. AIDS, June 20–24, San Francisco, Abstract Th.A. 284 (Japanese isolate); Phillips et at. (1990) J. Virol. 64:4605–4613 (San Diego, Calif.); Olmsted et al. (1989) Proc. Natl. Acad. Sci. USA 86:2448–2452 (Petaluma, Calif.); Talbot et al. (1989) Proc. Natl. Acad. Sci. USA 86:5743–5747 (Petaluma, Calif.); Rigby et al. (1991) In: Proc. Intnl. Feline Immunology and Immunodeficiency Workshop, Cameron House, Loch Lomand, Scotland, May 28–31, page 42 (Scotland); and Siebelink et al. (1991) In: Proc. Intnl. Feline Immunology and Immunodeficiency Workship, supra. (The Netherlands). Any of these isolates could be used for preparing vaccines and cell lines according to the present invention.

FIV encodes an RNA-dependent DNA polymerase (reverse transcriptase) which is $Mg^{+2}$-dependent with maximal activity occurring at a $Mg^{+2}$ concentration of approximately 5 mM and pH of approximately 7.8. FIV bands at a density of about 1.15 $gcm^3$ in a continuous sucrose gradient. Western blotting of FIV-infected cell lysate yields major bands at approximately 22 to 28 kD, usually about 26 kD; 50 to 60 kD, usually about 55 kD; and 28 to 36 kD, usually about 32 kD.

FIV may be isolated from the sera of infected cats by conventional techniques. For example, peripheral blood lymphocytes (PBL) may be isolated from the blood of infected cats and placed in suitable culture media. The cultures are incubated, with normal PBL's being periodically introduced to the culture in order to maintain its viability as the original cells are killed by the virus. The infected cells should be placed in fresh culture medium periodically, and the virus may be recovered from the supernatant of the cell culture by sucrose-gradient separation, or other known separation techniques.

The FIV may also be obtained from other specimens, particularly from the lymph tissues of infected animals. The lymph tissues are broken and then suspended in culture medium, and the procedures described above are then carried out.

Compositions according to the present invention include the whole virus, as well as portions of the virus. The whole virus may be maintained in in vitro culture, as described above, or may be viably frozen at a temperature at or below about −78° C. (solid $CO_2$-dry ice), usually in the presence of agents which promote amorphous, vitreous solidification rather than crystallization. Suitable agents include glycerol and dimethylsulfoxide. Portions of the FIV of particular interest include the structural and regulatory proteins encoded by the FIV genome, including the envelope and core proteins, and fragments thereof.

The FIV may also be maintained in chronically infected cell lines, particularly T-cell lines, as described in detail in the Experimental section hereinafter. For example, interleukin 2 (IL-2)-dependent T-cell lines can be infected with FIV and maintained in IL-2-supplemented culture media. IL-2-independent cell lines can then be prepared by repeated subculturing with a gradual depletion of IL-2. Surviving cultures can then be maintained in culture free from IL-2. The IL-2independent FIV-infected cell lines have been found to possess enhanced viability and a reduced percentage of syncytial cells when compared to IL-2-dependent FIV-infected cell lines. See, Experimental section hereinafter.

The FIV used for infecting the cell lines may be isolated from infected cats, as described above, or may be obtained from the deposited Petaluma strain of the virus (A.T.C.C. VR 2186).

Particular non-infected feline T-lymphocyte cell lines (IL-2 dependent) which may be infected to produce chronically FIV-infected cell lines are designated FeT-1M (A.T.C.C. Accession No. CRL 10775) and FeT-2D (A.T.C.C. Accession No. CRL 10774), both deposited at the American Type Culture Collection, 12301 Parklawn Drive, Rockville, Md., on Jun. 7, 1991.

Particular FIV-infected cell lines (IL-2 independent) which have been established from FeT-1M are FL-4 (A.T.C.C. Accession No. CRL 10772) and FL-6 (A.T.C.C. Accession No. CRL 10773), both deposited at the American Type Culture Collection on Jun. 7, 1991. Both these cell lines have been found to be prolific producers of FIV.

FeT-1M, FeT-2D, FL-4 and FL-6 were developed in the laboratory of Dr. Janet K. Yamamoto at the University of California, Davis, Calif.

Polypeptides of the present invention will be either haptenic or antigenic, including at least six amino acids, usually at least nine amino acids, and more usually twelve or more amino acids found contiguously within one of the natural FIV proteins. Polypeptides will generally correspond to at least one epitopic site which is characteristic of FIV. By characteristic, it is meant that the epitopic site will allow immunologic detection of the virus in a physiological sample with reasonable assurance. Usually, it will be desirable that the epitopic site be immunologically distinct from (i.e., not cross-reactive with antibodies which recognize) viruses other than FIV. In some cases, however, it may be desirable that the epitopic site be immunologically similar to other viruses.

The FIV polypeptides may be natural, i.e., including the entire FIV protein or fragments thereof isolated from a natural source, or may be synthetic. The natural polypeptides may be isolated from the whole virus which is obtained as describe above by conventional techniques, such as affinity chromatography. Conveniently, polyclonal or monoclonal antibodies obtained according to the present invention (as described in more detail hereinbelow) may be used to prepare a suitable affinity column by well-known techniques. Such techniques are taught, for example, in Hudson and Hay, *Practical Immunology*, Blackwell Scientific Publications, Oxford, United Kingdom, 1980, Chapter 8.

Synthetic polypeptides which are immunologically cross-reactive with a natural FIV protein may be produced by either of two general approaches. First, polypeptides having fewer than about 100 amino acids, more usually fewer than about 80 amino acids, and typically fewer than about 50 amino acids, may be synthesized by the well-known Merrifield solid-phase synthesis method where amino acids are sequentially added to a growing chain (Merrifield (1963) J. Am. Chem. Soc., 85:2149–2156).

The second and preferred method for synthesizing the polypeptides of the present invention involves the expression in cultured cells of recombinant DNA molecules encoding a desired portion of the FIV genome. The portion of the FIV genome may itself be natural or synthetic, with natural genes obtainable from the isolated virus by conventional techniques. Of course, the genome of FIV is RNA, and it will be necessary to transcribe the natural RNA into DNA by conventional techniques employing reverse transcriptase. Alternatively, polynucleotides may be synthesized by well-known techniques. For example, short single-stranded DNA fragments may be prepared by the phosphoramidite method described by Beaucage and Carruthers (1981), Tett. Letters 22:1859–1862. Double-stranded fragments may then be obtained either by synthesizing the complementary strand and then annealing the strands together under appropriate conditions, or by adding the complementary strand using DNA polymerase with an appropriate primer sequence.

The natural or synthetic DNA fragments coding for the desired FIV protein or fragment may be incorporated in a DNA construct capable of introduction to and expression in in vitro cell culture. Usually, the DNA constructs will be suitable for replication in a unicellular host, such as yeast or bacteria. They may also be intended for introduction and integration within the genome of cultured mammalian or other eukaryotic cells. DNA constructs prepared for introduction into bacteria or yeast will include a replication system recognized by the host, the FIV DNA fragment encoding the desired polypeptide product, transcriptional and translational initiation regulatory sequences joined to the 5'-end of the FIV DNA fragment, and transcriptional and translational termination regulatory sequences joined to the 3'-end of the fragment. The transcriptional regulatory sequences will include a heterologous promoter which is recognized by the host. Conveniently, a variety of suitable expression vectors are commercially available for a number of hosts.

To be useful in the detection methods of the present invention, the polypeptides are obtained in a substantially pure form, that is, typically from about 50% W/W or more purity, substantially free of interfering proteins and contaminants. Preferably, the FIV polypeptides are isolated or synthesized in a purity of at least 80% W/W, and more preferably, in at least about 95% W/W purity. Using conventional protein purification techniques, homogeneous polypeptide compositions of at least about 99% W/W purity can be obtained. For example, the proteins may be purified by use of the antibodies described hereinafter using the immunoabsorbant affinity columns described hereinabove.

Once a sufficient quantity of natural or synthetic FIV polypeptides have been obtained, polyclonal antibodies specific for FIV may be produced by in vitro or in vivo techniques. In vitro techniques involved in vitro exposure lymphocytes to the antigenic polypeptides, while in vivo techniques require the injection of the polypeptides into a wide variety of vertebrates. Suitable vertebrates are non-human, including mice, rats, rabbits, sheep, goats, and the like. Polypeptides having more than about thirty amino acids, usually more than about fifty amino acids, may serve directly as the immunogen. If the polypeptide is smaller than about 10 kD, particularly less than about 6 kD, however, it may be necessary to join the polypeptide to a larger molecule to elicit the desired immune response. The immunogens are then injected into the animal according to a predetermined schedule, and the animals are bled periodically with successive bleeds having improved titer and specificity. Injections may be made intramuscularly, subcutaneously, or the like, and an adjuvant, such as a combination of complete and incomplete Freund's adjuvant, will usually be employed. The whole virus can also be used as the immunogen, although selection of antibodies specific for a particular determinant will be more difficult.

If desired, monoclonal antibodies can be obtained by preparing immortalized cell lines capable of producing antibodies having the desired specificity. Such immortalized cell lines may be produced in a variety of ways. Conveniently, a small vertebrate, such as a mouse, is hyperimmunized with the desired antigen by the method just described. The vertebrate is then killed, usually several days after the final immunization, the spleen removed, and the spleen cells immortalized. The manner of immortalization is not critical. Presently, the most common technique is fusion with a myeloma cell fusion partner, as first described by Kohler and Milstein (1976) Eur. J. Immunol. 6:511–519. Other techniques include EBV transformation, transformation with oncogenes, retroviruses, etc., or any other method which provides for stable maintenance of the cell line and production of monoclonal antibodies.

When employing fusion with a fusion partner, the manner of fusion is not critical and various techniques may be employed. Conveniently, the spleen cells and myeloma cells are combined in the presence of a non-ionic detergent, usually polyethylene glycol, and other additives such as Dulbecco's Modified Eagle's medium, for a few minutes. At the end of the fusion, the non-ionic detergent is rapidly removed by washing the cells. The fused cells are promptly dispensed in small culture wells (usually in a microtiter plate at relatively low density, ranging from about one to $5 \times 10^5$ cells/well), in a selective medium chosen to support growth of the hybrid cells while being lethal to the myeloma cells. Usually, the myeloma cell line has been mutated to be sensitive to a lethal agent, typically being HAT sensitive, and the medium includes a HAT concentration sufficient to inhibit the proliferation of the unused myeloma cells.

After sufficient time, usually from about one to two weeks, colonies of hybrids are observed and plates containing hyperpositive wells are identified. The plates and wells having only one colony per well are selected, and supernatants from these wells are tested for binding activity against FIV or a particular FIV protein. Once positive hybridomas are identified, the cell line can be maintained as a viable culture and/or a quantity of the virus may be grown out, separated, and stored by lyophilization.

Depending on the desired use for the antibodies, further screening of the hybridomas may be desirable. For use in immunodiagnostic assays, antibodies having very high specificity and affinity for the antigenic site are desirable.

Once the desired hybridomas have been selected, monoclonal antibodies may be isolated from supernatants of the growing colonies. The yield of antibodies obtained however, is usually low. The yield may be enhanced by various techniques, such as injection of the hybridoma cell line into the peritoneal cavity of a vertebrate host. Monoclonal antibodies may then be harvested from the ascites fluid or the blood. Proteinaceous and other contaminants will usually be removed from the monoclonal antibodies prior to use by conventional techniques, e.g., chromatography, gel filtration, precipitation, extraction, or the like.

The polypeptides and antibodies of the present invention may be used with or without modification for the detection of or vaccination against FIV infection. Frequently, the polypeptides and antibodies will be labelled by joining, either covalently or non-covalently, a substance which provides for detectable signal. A wide variety of labels and conjugation techniques are known and are reported extensively in both the scientific and patent literature. Some of the labels include radionuclides, enzymes, substrates, cofactors, inhibitors, fluorescers, chemiluminescers, magnetic particles and the like. Patents teaching the use of such labels include U.S. Pat. Nos. 3,817,837; 3,850,752; 3,939,350; 3,996,345; 4,277,437; 4,275,149; and 4,366,241.

Antibodies and polypeptides prepared as described above can be used in various immunological techniques for detecting FIV and anti-FIV antibodies in physiological specimens, particularly body fluid samples, including blood, plasma, serum, urine, and the like, and cell samples, such as lymphocytes. Depending on the nature of the sample, both immunoassays and immunohistochemical staining techniques may find use.

Liquid phase immunoassays and Western blot analysis will find use in detection of FIV in body fluids, particularly blood and urine. The use of antibodies in protein binding assays is well established. Numerous competitive and noncompetitive protein binding assays have been described in the scientific and patent literature, and a large number of such assays are commercially available. Detailed methods for detecting the presence of the viruses in serum samples are set forth in the Experimental section hereinafter. Additionally, enzyme linked immunosorbent assays (ELISA) for detecting presence of antibodies to FIV in blood are also set forth in the Experimental section.

Compositions of the present invention are also useful in preparing vaccines for protection against FIV infection. For example, the whole virus and/or FIV-infected cell lines may be wholly or partially inactivated and utilized as an immunogen in a vaccine composition. Partial inactivation may be achieved by passage at elevated temperatures or by contact with mutagens, such as ultraviolet light, ethyl methanesulfonate, and the like. Complete inactivation may be achieved by contact with other agents, including formalin, paraformaldehyde, phenol, α-lactopropionate, ultraviolet light, heat, psorlens, platinum complexes, ozone and other viricidal agents.

Specific methods for the preparation of inactivated whole virus and FIV-infected cell line vaccines are described in detail in the Experimental section hereinafter. Conveniently, the source of whole FIV can be FIV-infected cell lines which have been found to be prolific producers, such as FL-4 and FL-6. Inactivated FL-4 and FL-6 are also suitable for preparing inactivated or attenuated whole cell vaccines.

The viral proteins and portions thereof, prepared as described above, may also be used in the preparation of subunit vaccines prepared by known techniques. Polypeptides displaying antigenic regions capable of eliciting protective immune response are selected and incorporated in an appropriate carrier. Alternatively, an antigenic portion of a viral protein or proteins may be incorporated into a larger protein by expression of fused proteins. The preparation of subunit vaccines for other viruses is described in various references, including Lerner et al. (1981) Proc. Natl. Acad. Sci. USA 78:3403 and Bhatanagar et al. (1982) Proc. Natl. Acad. Sci. USA 79:4400. See also, U.S. Pat. Nos. 4,565,697 (where a naturally-derived viral protein is incorporated into a vaccine composition); 4,528,217 and 4,575,495 (where synthetic peptides forming a portion of a viral protein are incorporated into a vaccine composition). Other methods for forming vaccines employing only a portion of the viral proteins are described in U.S. Pat. Nos. 4,552,757; 4,552,758; and 4,593,002. The relevant portions of each of these cited references and patents are incorporated herein by reference.

The vaccines prepared as described above may be administered in any conventional manner, including oranasally, subcutaneously, intraperitoneally or intramuscularly, except that oronasal administration will usually not be employed with a partially inactivated virus vaccine. Adjuvants will also find use with subcutaneous and intramuscular injection of completely inactivated vaccines to enhance the immune response. The preparation of viral vaccine compositions optionally employing adjuvants is described in numerous standard references, such as *Remington's Pharmaceutical Sciences,* Mack Publishing Co., Easton, Pa., 16th ed., 1982, the disclosure of which is incorporated herein by reference.

The dosage form and immunogen content of the vaccine will vary depending on the nature of the immunogen (i.e., whole virus, infected cell, or subunit) and the route of administration. Usually, a single dose will have a total volume including carrier, adjuvant, and any other components, in the range from about 0.1 ml to about 5 ml, more usually being from about 0.5 ml, more usually being from about 0.5 ml to about 3 ml. The amount of inactivated or attenuated whole FIV in each dose will usually be in the range from about 0.1 mg to about 5 mg, usually being from about 0.2 mg to 2 mg. For inactivated FIV-infected cell lines, each dose will typically contain from about $10^6$ to $10^8$ cells, usually about $5\times10^6$ to $5\times10^7$ cells.

The number and temporal spacings of the inoculations will be sufficient to elicit the desired immunoprotective response against subsequent challenge by FIV. Usually, there will be at least two inoculations spaced at least one week apart, more usually being from two to 10 inoculations spaced over a period from two to thirty weeks. Often, a final inoculation may be administered at some longer interval following an initial series of administrations. The selection of optimum administration patterns for a particular vaccine formulation is well within the skill in the art.

Diagnostic tests for detecting the presence of FIV in biological samples may also be performed using polynucleotide probes. Such polynucleotide probes may be prepared based on the sequence of the viral genome. The length of the probe is not critical, but will usually comprise at least about 12 bases, more usually comprising at least about 16 bases, which are substantially complementary to a portion of the viral genome. The probe itself may be DNA or RNA, and the probe need not have perfect complementarity with the FIV genome, with one or two mismatched pairs being acceptable for probes up to 20 bases in length and three to five mismatched pairs in probes from 20 to 35 bases. The probes may be prepared synthetically, with suitable synthetic techniques having been described above, and will include a detectable label. Usually, the synthetic sequences are expanded in commonly available cloning vectors and suitable hosts in order to obtain large quantities. The expanded vectors may themselves be labelled for use as probes, or shorter fragments containing complementary strands may be excised and labelled. Methods for the preparation and utilization of nucleotide probes for diagnostic testing are described in Falkow et al. U.S. Pat. No. 4,358,535, the disclosure of which is incorporated herein by reference.

A variety of labels have been employed, including those which have been described above for use in immunoassays, particularly radionuclides. Suitable labels may be bound to the probe by a variety of techniques. Commonly employed is nick translation with $\alpha\text{-}^{32}P\text{-}dNTP$ terminal phosphate hydrolysis with alkaline phosphatase followed by 5'-end labelling with radioactive $^{32}P$ employing $\gamma\text{-}^{32}P\text{-}NTP$ and T4 polynucleotide kinase or 3'-end labelling with an $\alpha\text{-}^{32}P\text{-}dNPT$ and terminal deoxynucleotidyl transferase. Alternatively, nucleotides can be synthesized where one or more of the atoms present are replaced with a radioactive isotope, e.g., hydrogen with tritium. In addition, various linking groups can be employed. The terminal hydroxol can be esterified with inorganic acids, e.g., $^{32}p$ phosphate or $^{14}C$ organic acids, or else esterified with bifunctional reagents to provide other reactive groups to which labels can be linked.

The following examples are offered by way of illustration, not by way of limitation.

The experimental work described below relating to the development and use of cell lines FeT-1M, FeT-2D, FL-4, and FL-6 was performed in the laboratory of Dr. Janet K. Yamamoto at the University of California, Davis, Calif..

EXPERIMENTAL

Materials and Methods

Cell Types

Cells used as the source of FIV were the Crandell feline kidney cell line (FIV-CRFK) and feline mixed fresh PBLs (FIV-FeT1). Both cell types were infected with the Petaluma strain of FIV (A.T.C.C. No. VR 2186; deposited on Aug. 5, 1987, in connection with parent application serial number 07/089,700). The FIV-CRFK line grows as a monolayer, morphologically similar to uninfected CRFK cells (Yamamoto et al. (1988) Am. J. Vet. Res. 49:1246–1258 and Fabricant et al. (1971) J. Am. Vet. Med. Assoc.

158:976–980). FIV-FeT1 cells, like uninfected FeT1 cells (mixed peripheral blood lymphocyte (PBL) cells from specific pathogen free (SPF) cats), grow in suspension and require interleukin-2 (IL-2). The IL-2 -independent feline leukocyte cell lines, FL-4 and FL-6, were derived from the FIV-FeT1 cells and also are suspension cells which spontaneously produce FIV.

Cell Cultures

All suspension cell lines used in this study (FeT1, FL-4, FL-6) were cultured in RPMI 1640 containing 10% heat-inactivated fetal calf serum (FCS), 10 mM HEPES (N-2-hydroxyethylpiperazine-n'-2-ethane sulfonic acid), 2 mM L-glutamine, 50 µg/ml gentamicin, and $5 \times 10^{-5}$M 2-mercaptoethanol. IL-2-dependent cells were supplemented with 100 U/ml of recombinant human IL-2 (Cetus Corporation, Emeryville, Calif.). The suspension cells were passaged at a cell concentration of $0.5-4 \times 10^6$ cells/ml and recultured in fresh culture media twice a week. FIV-CRFK cells were cultured in media consisting of equal volumes of L-15 and Eagle's minimum essential media, 10% heat-inactivated FCS, and 50 µg/ml gentamicin. All monolayer cells were passaged twice a week at an initial cell concentration of $2 \times 10^6$ cells/ml. The FIV-infected tissue culture fluids (TCF) were harvested twice a week, spun at 3000 rpm for 1 hr to remove residual cells, and stored at $-20°$ C. or $-70°$ C. or at $5°$ C. for those scheduled to be used within 1–5 days. One ml samples of cell-free infected TCF were routinely tested for $Mg^{++}$-dependent reverse transcriptase (RT) activity as a means of monitoring for FIV production. Infected TCF were also checked routinely for $Mn^{++}$-dependent RT activity to ensure that the cultures were producing only $Mg^{++}$-dependent feline retrovirus (i.e., FIV). The RT assay used poly(rA)-oligo($dT_{12-18}$) as an exogenous template primer, four different deoxyribonucleotide triphosphates, 20 mM KCl with $Mg^{++}$ for detecting FIV or 60 mM NaCl with $Mn^{++}$ for detecting $Mn^{++}$-dependent viruses (such as FeLV) and 5 µCi ($^3$H)TTP alone per sample (Rey et al. (1984) Biophys. Res. Commun. 121:126–133). Five µCi of ($^3$H)TTP gave an average total count of 450,000 cpm using scintillation fluid mixture (1 part xylene to 2 part Amersham biodegradable counting scintillant) on a Bechman LS250 scintillation counter. As a result, our RT values will be below 450,000 cpm/ml.

Development of IL-2-Independent FIV Producer Lines

IL-2-independent FIV producing cell lines were developed from an IL-2-dependent FIV-infected feline PBL line ( FIV-FeT1 ) . The process of gradual IL-2 depletion from the FIV-FeT1 cell line took extensive sub-culturing over a period of approximately three months. The depletion process entailed a gradual reduction of the percentage of IL-2 containing media from the culture in the following weekly sequence: 75% 50%, 25% 5% and 0% IL-2-containing media. During this period over 80% of the starting cultures which were depleted of IL-2 did not survive the procedure. Surviving cultures were placed in individual 2-cm$^2$ multi-wells at a viable cell concentration of $2 \times 10^6$ cells/ml/well. During this stage only three of starting 20 cultures survived and these cultures were expanded sequentially into 25-cm$^2$, 75-cm$^2$, and 175-cm$^2$ flasks. One of the cultures (FL-5) did not survive. RT assays were performed on the surviving two cultures (FL-4 and FL-6) during the expansion period as means of monitoring FIV production.

In Vitro Infectivity Studies

The clarified infectious TCF from FL-4, FL-6, FIV-FeT1, and FIV-CRFK cells was filtered individually with 0.45 µm sterile filters to remove residual cells. These FIV inocula were aliquoted into 8-ml samples, stored at $-70°$ C. and samples of these frozen inocula were retested for RT activity prior to in vitro infectivity studies. In all studies, the frozen inocula were thawed at room temperature immediately prior to use. FIV-susceptible feline cells ($1 \times 10^6$ cells/ml) were infected with FIV at RT activity of 30,000 cpm/ml. All of the FIV-susceptible cells used in this study, with the exception of uninfected CRFK, were IL-2-dependent lymphoid cells which grew in suspension and required no trypsinization for passage. The TCF of the infected test cultures was harvested twice a week and the cells were recultured in fresh culture media containing IL-2. The harvested TCF was routinely tested for RT activity.

In Vivo Infectivity Studies

Two specific pathogen fee (SPF) cats, 11 months of age, were inoculated intraperitoneally (IP) with 2 ml of infectious TCF from either FL-4 or FL-6 cells. Infectious TCF from FL-4 or FL-6 cultures, having RT activities of 150,000 cpm/ml, was aliquoted and stored at $-70°$ C. The frozen virus inocula were thawed at room temperature and filtered with 0.45 µm Millipore filter just prior to the inoculation. Both the single freeze-thawing and the filtering procedure ensured that the inocula were free of viable cells. The cats were bled routinely to obtain serum for serological assays and PBLs for virus isolation. Virus isolation consisted of cocultivating $2-10 \times 10^5$ cells/ml with equal number of FIV-susceptible uninfected FeT1 cells and monitoring the TCF from these cultures for six weeks by RT assay. The PBL were considered positive for FIV isolation when RT activity of >10,000 cpm/ml were detected in TCF from at least two consecutive harvest days. The RT activity of the TCF from co-culturing PBL from SPF cats with FeT1 cells was <2,500 cpm/ml.

FIV Purification

FIV from infected TCF was concentrated and purified by ultracentrifugation, first on a 10/50% (w,v) discontinuous sucrose gradient and then on a 10/50% continuous sucrose gradient (Pedersen et al. (1987) Science 235:790–793 and Yamamoto et al. (1988) Leukemia, December Supplement 2:204S–215S). The virus purified by this procedure was used for comparing the biochemical properties of FIV derived from different culture preparations and as the viral substrate for the immunoblot assay. Immunoblot analyses of gradient purified FIV from different infected cell lines (FL-4, FL-6, FIV-FeT1, and FIV-CRFK cells) demonstrated the presence of the envelope gp100 band in blots from all viral sources. However, one major difference observed during these studies was that the intensity of the gp100 band was always weaker on the immunoblots made from purified FIV of FIV-CRFK origin than from those produced by other infected cell lines. Consequently, more viral antigen from FIV-CRFK cells was needed on the blots to get comparable intensity at the envelope band.

Immunoblot Analysis

A modification of the immunoblot technique described by Carlson et al. was used (Carlson et al. (1985) JAMA 253:3405–3408). Serum samples from immunized or FIV-infected cats were diluted to 1:50 in Buffer 3 (0.15M sodium chloride, 0.001M ethylene diamintetraacetic acid, 0.05M Tris base, 0.05% Tween 20, and 0.1% bovine serum albumin) and incubated with the virus blot strips in individual wells for 18 hours at 37° C. These blot strips were then processed using a modification of a previously described procedure (Yamamoto et al. (1988) supra.). Briefly, the strips were incubated individually in wells with biotinylated anti-cat IgG (Vector Laboratories, Burlingame, Calif.) for 30 min and washed three times with wash solution. The strips were then incubated individually with horseradish peroxidase Avidin D (Vector Laboratories) for 30 min. After extensive washing, the strips were incubated with a fresh substrate solution (0.05% diaminobenzidine, 400 μg/ml $NiCl_2$ and 0.01% $H_2O_2$ in 0.1M Tris buffer, pH 7.4) at room temperature. After establishment of visible bands the reactions were stopped with excess distilled $H_2O$, and the strips were then dried.

FIV p28 Assay

The FIV core protein p28 was detected by an enzyme-linked immunoadsorbent assay (ELISA) using two different monoclonal antibodies. A1 and B1 mAbs, to FIV p28 as either capture or substrate-reactive antibodies, respectively. Reactivity of both mAbs to FIV p28 antigen was confirmed by immunoblot analysis. The capture antibody (mAb A1) was coated on the plate overnight with bicarbonate buffer (pH 9.6) and washed once before its use. Serum samples to be tested were diluted in Buffer 3 and then incubated in the coated wells for 30 min at 37° C. The wells were washed six times with washing buffer, incubated with biotinylated mAb B1 for 30 min at 37° C., washed six times more, and then incubated with horseradish peroxidase Avidin D for 15 min. The wells were washed extensively again and finally incubated with substrate solution (0.005% tetramethylbenzidine and 0.015% $H_2O_2$ in 0.96% citric acid solution) at room temperature. The reactions were stopped with 1M sulfuric acid solution upon establishment of a visible color reaction in the sequentially diluted standards consisting of purified FIV from pooled FIV-CRFK and FIV-FeT1 preparations.

Characterization of FL-4 and FL-6 Cell Lines

The phenotypic profiles of the feline cells were determined by fluorescence activated cell sorter (FACS) analysis using characterized monoclonal antibodies to feline CD4 (Fel 7), CD8 (FT2), pan T-cell, and to feline light chain and μ heavy chain specific (AC5) markers (Ackley et al. (1990) supra.; Ackley et al. (1990) supra.; Klotz et al. (1986) J. Immunol. 136:2510–2516; and Klotz et al. (1985) J. Immunol. 134:95–99). The cells were tested for mycoplasma using two different procedures both performed by Bionique Laboratories, Inc. The first procedure consisted of the direct DNA/fluorochrome staining of the cells for mycoplasma. The second procedure involved passaging test cells onto indicator cells which were then DNA/fluorochrome stained for mycoplasma. Detection of FeLV p27 core antigen was performed using the p27 antigen ELISA assay (Lutz et al. (1983) J. Immunol. Methods 56:209–220). Polymerase chain reaction (PCR) was used to test for the presence of FeLV provirus DNA. Briefly, a pair of primer sequences from the U3 region of the FeLV LTR were chosen so as to avoid the possibility of overlap with endogenous sequences of FeLV. The sequences of the two oligonucleotides primers used for PCR were 14 base pairs (bp 24 to 37) and 17 base pairs (bp 239 to 255) long. This enabled us to amplify a sequence of 232 base pairs for which we prepared a 25 base pair probe (bp 203 to 227) labeled with $^{32}P$ for identification by Southern blotting. The indirect fluorescent antibody assay to detect feline syncytium-forming virus (FeSFV) was performed as described previously (Pedersen et al. (1987) supra.; Yamamoto et al. (1988) supra.; and Yamamoto et al. (1989) J. Am. Vet. Med. Assoc. 194:213–220).

Immunogenicity of FIV Produced from FL-4 and FL-6 Cells

Eighteen SPF cats, 4–6 months of age, were used in these studies. Some of these cats were previously exposed to feline herpes virus (FHV)(A.T.C.C. C-27 strain) and the cats were free of FHV symptoms two-weeks prior to and during immunization. Three of the cats were immunized four times with 200 μg of inactivated FIV (inactivated whole virus) particles that were produced by pelleting cell-free TCF of FL-4 cells. An additional three cats were immunized eight times with 20 μg of inactivated whole virus. Seven cats were immunized either four or six times with $1 \times 10^7$ cells per dose of inactivated FL-6 or FL-4 cells (inactivated whole cell-virus), respectively. The pelleted virus and the infected cells were each inactivated with 1.25% paraformaldehyde, dialyzed against PBS, and then combined with adjuvant just prior to immunization. The adjuvants used were either threonyl muramyl dipeptide (MDP) (Byars et al. (1987) Vaccine 5:223–228) or a combination of Freund's complete and incomplete adjuvants. Control cats were immunized with either uninfected FeT1 cells with adjuvant or diluent with adjuvant. All cats were immunized at two week intervals for a total of four or eight immunizations, unless stated otherwise.

RESULTS

Development of IL-2-Independent FIV-Producing Cell Lines

The development of IL-2-independent cell lines from FIV infected mixed PBLs (FIV-FeT1 cells) entailed the gradual depletion of IL-2 from the cultures. Only two out of 20 cultures, FL-4 and FL-6, survived the depletion process. Significant RT titers (100,000–400,000 cpm/ml), $Mg^{++}$ cation-dependent, were detected in these cultures during the expansion and large scale-production stage. Electron microscopy demonstrated numerous typical lentivirus particles in these cultures (data not shown).

The growth rates of these cell lines were compared to those of FIV-FeT1 and FIV-CRFK. The viable cell doubling time for FL-6 was found to be approximately 24 hours, whereas the doubling time for FL-6 was found to be approximately 24 hrs, whereas the doubling time for FL-4 was approximately 48 hrs. Both cell lines grew at an exponential rate. From a starting cell concentration of $5 \times 10^5$ cells/ml, peak viable cell counts were observed after 3–4 days of culturing. Viability of the cells present in these cultures ranged from 70 to 90% over the four day culturing period. The number of syncytial cells in the FL-4 and FL-6 cultures was less than 0.1%. In comparison, the viability of FIV-FeT1 cells was only 55 to 65% after 1 day of culture, which may be attributed to dependence on IL-2. In our hands, a majority of the IL2-dependent feline (FeT1, FeT2) and murine (HT-2C, CTLL-2) lymphoid cell lines have similar viability profiles. In order to evaluate the correlation between cell growth and virus production, samples from different harvest days were assayed for RT activity (FIG. 1). At a starting cell concentration of $5 \times 10^5$ cells/ml, peak RT titers were observed on Day 4 of culture. Based on the number of cells present on Day 4, FL-4 cells produced the highest and FIV-CRFK the lowest RT activity.

Characterization of the FL-4 and FL-6 Cell Lines

The phenotypic profiles of FL-4 and FL-6 cells were determined by flow cytometric analysis using monoclonal antibodies (mAb) to feline CD4 (fel 7), CD8 (FT2), pan T-cell (42) markers (Ackley et al. (1990) J. Virol. 64:5652–5655; Carlson et al. (1985) supra.; Ackley et al. (1990) supra.; and Klotz et al. (1986) supra.) and mAb that detect both feline immunoglobulin light chains and µ heavy chain (AC5) (Klotz et al. (1985) supra.) (FIG. 2). The FACS profiles demonstrated that FL-4 cells were CD4$^\pm$, CD8$^+$, and Pan-T$^+$ whereas FL-6 cells were CD4$^-$, CD8$^\pm$, and Pan-T$^+$. Both cell lines were negative for surface IgM and λ and κ light chains. It should be noted that both CD4 and CD8 antigens were lost in cultures maintained for several months. FL-4 and FL-6 cells were >95% positive by IFA for surface FIV antigen expression using polyclonal antibodies to FIV (Table 1). Additional tests were performed to ensure that these cells were free of known contaminants which could limit their use. The results are summarized in Table 1. The two cell lines were mycoplasma-free both by direct DNA/fluorochrome stain and indirectly by passaging onto indicator cells prior to staining. Furthermore, FL-4 and FL-6 cells were shown to be negative for FeLV core protein p27 expression by ELISA and for exogenous FeLV DNA by PCR. The cells were determined to be negative by IFA for feline syncytial-forming virus (FeSFV).

TABLE 1

Absence of Known Contaminants in FL-4 and FL-6 Cell Lines

| Microorganism Tested | Infection Status | Antigen Detected | Method of Testing |
|---|---|---|---|
| FIV | + | viral RT[a] | Mg$^{++}$-dependent RT |
| | + | viral antigens[a,b] | Immunoblot analysis with FIV-positive serum. |
| | + | mature virion | Electron microscopy. |
| | + | whole cell | IFA with FIV-positive serum (>95% positive). |
| FeLV | – | viral RT[a] | Mn$^{++}$-dependent RT |
| | – | viral core p27 | ELISA. |
| | – | mature virion | Electron microscopy. |
| | – | proviral LTR sequence in cellular DNA | PCR and Southern blot. |
| FeSFV | – | mature virion | Electron microscopy. |
| | – | whole cell | IFA with FeSFV-positive serum. |
| Mycoplasma | – | whole cell | Direct DNA/fluorochrome staining for mycoplasma. Indirectly by staining indicator cells which were passaged with FL-4 and FL-6 cells. |

[a]These tests were performed on the tissue culture fluid harvested from the FL-4 and FL-6 cell cultures.
[b]Purified virus was disrupted with 0.1% SDS prior to its use in immunoblot production, as described in Methods.

FIV Production in FL-4 and FL-6 Cell Lines

The amount of FIV produced from the FL-4, FL-6, FIV-FeT1 and FIV-CRFK cell lines was determined by comparing the total protein and RT levels of FIV in different fractions from sucrose gradient preparations (data not shown). High titers of both RT activity and total protein were observed in FIV preparations from FL-4, FL-6, and FIV-FeT1 cells. The FIV-CRFK produced low titers of FIV as demonstrated by the low levels of both protein concentration and RT activity in the fractions. The three peak fractions of the gradient purified virus from each cell line were pooled and measured for total protein concentration, RT titer, and viral core protein (p28) concentration. The results demonstrated a direct correlation between the p28, RT and the total protein levels present in the purified virus preparations. The viral antigen profiles of the FIV produced by the various cell lines were also compared by immunoblot analysis. Different concentrations of purified virus from different cell sources were used as substrate antigen for immunoblot strips. These immunoblots were then reacted with a set concentration of FIV-seropositive cat sera and the banding patterns evaluated. The immunoblot profiles from FL-4 and FL-6 cells were similar to those of FIV-FeT1 and FIV-CRFK (data not shown). The intensity of the bands, especially the viral envelope and transmembrane glycoproteins, produced on immunoblots from FL-4, FL-6 and FIV-FeT1 viral substrates was stronger than that from FIV-CRFK. In addition, immunoblots of significantly higher quality were produced from the larger quantity of purified virus obtained from the TCF of FL-4 and FL-6. Thus, these results further indicate that a larger amount of virus antigens was produced by the FL-4 and FL-6 cell lines than by the FIV-FeT1 and FIV-CRFK.

Characterization of FIV Produced From FL-4 and FL-6 Cells

Figure 4:
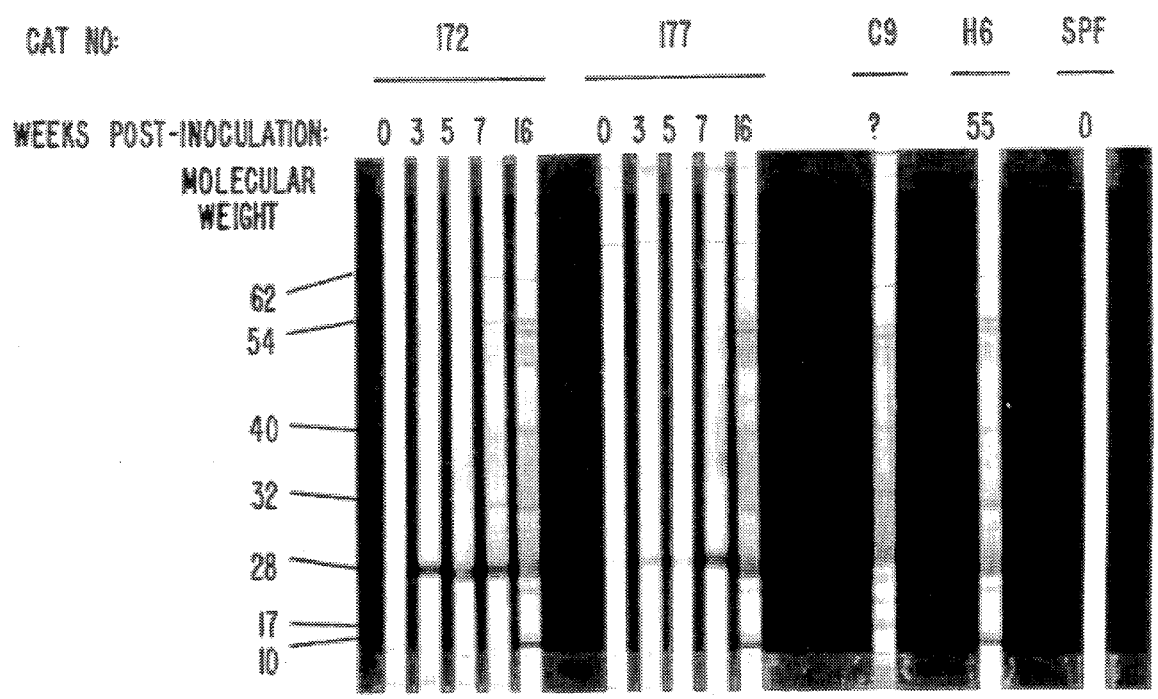

The FIV produced from FL-4 and FL-6 cells was tested for its ability to infect FIV-susceptible cell lines (FIG. 3). Cell-free TCF from different infected cell lines was inoculated into various feline cell cultures at a set RT concentration of 30,000 cpm/ml. FIV from FIV-CRFK cells did not readily infect certain feline lymphoid cells, in particular thymus-derived cultures, as compared to the FIV from FL-4 and FIV-FeT1 cells. The FIV from FL-6 cells was also highly infectious to FIV-susceptible cell lines (data not shown). Next, the FIV preparations produced from FL-4 and FL-6 cells were tested for their ability to infect SPF cats (FIG. 4). One SPF cat each was inoculated IP with 2 ml of cell-free TCF from either FL-4 or FL-6 cells. Both cats developed antibodies to FIV within four weeks post-infection. By sixteen weeks post-infection, the immunoblot profiles of these sera demonstrated the presence of antibodies to the majority of viral core antigens, but not to the viral envelope or transmembrane glycoproteins. Both cats were positive for virus isolation from PBLs. These studies demonstrated that the virus preparations from the FL-4 and FL-6 cell lines were highly infectious in both in vitro and in vivo systems.

Immunogenicity of FIV Produced From FL-4 and FL-6 Cells

Immunization of four cats with the inactivated FL-4 cell preparations (1×10$^7$ cells) led to the production of FIV antibodies specific for the viral core protein p28 soon after the second immunization (FIG. 5A). Antibodies to other viral antigens were demonstrated only after the third or fourth immunization (FIG. 5A). Thus the development of the antibodies in immunized cats closely mimics the FIV antibody development in experimentally infected cats (Yamamoto et al. (1988) supra. and Hosie et al. (1990) supra.). Control cats immunized with uninfected FeT1 cell preparations did not develop viral antibodies over the duration of the six immunizations.

Six other cats were immunized with inactivated FL-4-produced virus (200 μg) or inactivated FL-6 cell ($1\times10^7$ cells) preparations together with a combination of complete and incomplete Freund's adjuvant instead of MDP (FIG. 5B). Both inocula led to the production of antibodies specific to the viral p28 shortly after the second immunization. Two out of the three cats immunized with the inactivated virus preparation developed antibody responses to viral envelope, whereas all three cats immunized with the inactivated FL-6 cell preparation developed antibodies to the envelope shortly after the second immunization. When other cats were immunized with 20 μg of pelleted inactivated virus (in MDP) per dose, two out of three cats developed antibodies to the viral envelope, but only after the sixth immunization (FIG. 5B). Furthermore, $1\times10^7$ viable FL-4 or FL-6 cells released into the TCF approximately 10 μg equivalence of purified virus (by sucrose gradient method) or approximately 30 μg equivalence of crude pelleted virus when at their peak production level (data not shown). These findings suggest that it is more practical to use inactivated whole infected cells as an immunogen than inactivated whole virus for development of antibodies to the viral envelope. No difference in antibody development to viral p28 was observed between the infected cell or cell-free virus immunogens. Thus, our studies demonstrate that cats immunized with inactivated whole FIV-infected cells generate higher FIV envelope antibody titers more rapidly and more consistently than those immunized with inactivated cell-free whole virus.

Vaccination with Inactivated Cell Lines and Post Vaccination Challenge

The fixed cell-virus vaccine consisted of FIV-FeT1 and FIV-FL-4 inactivated with paraformaldehyde. In each culture (which was subsequently inactivated) essentially 100% of the cells were productively infected with FIV and $5\times10^7$ cells were required to obtain 100 μg of total viral protein. Analysis of the FIV-infected cells in both T-cell lines by immunoblot using serum from an FIV immunized cat and by Coomassie stain, showed that the vaccine preparations contained the env, gag and pol virion proteins and their precursors as well as some regulatory proteins and cellular proteins (data not shown). The adjuvant used was threonylmuramyl dipeptide (MDP) (Syntex SAF-A).

The infected cells were inactivated with 1.25% paraformaldehyde for 24 hrs and washed three times with phosphate buffered saline (PBS). The vaccine consisted of $1\times10^7$ inactivated FIV-FeT1 cells (Group 1A) or FIV-FL-4 cells (Group 1B) mixed with 250 μg of MDP. All cats in Group 1 were specific pathogen free (SPF) cats of 4–6 months of age, which were previously exposed to feline herpes virus (FHV C-27 strain) and were free of FHV symptoms two weeks prior to and during immunization. Ten control cats were immunized with either uninfected FeT1 cells with MDP (Group 1C) or MDP alone (Group 1D). All cats were challenged IP with 10 animal infectious doses ($AID_{100}$) of homologous FIV petaluma strain two weeks after the final immunization. For the whole-virus vaccine, FIV was pelleted from the culture fluid of FIV-FL-4 cells, inactivated with 1.25% paraformaldehyde for 24 hours, and dialyzed extensively against PBS. Cats in Group 2A were SPF cats which were immunized with the inactivated FIV particles. Group 2B cats received $1\times10^7$ inactivated uninfected FeT1 cells mixed with the inactivated virus. Three additional SPF cats were immunized with either adjuvant (Cat #182) or diluent (Cats #55D and #55H). All cats were challenged with 10 ID FIV (homologous strain) two weeks after the final immunization. Virus was isolated from PBL and bone marrow cells by co-culturing with FIV-susceptible FeT1 cells. PCR analysis was performed using the method previously described (Pedersen et al. (1989) J. Virol. 64:598–606).

Figure 7:
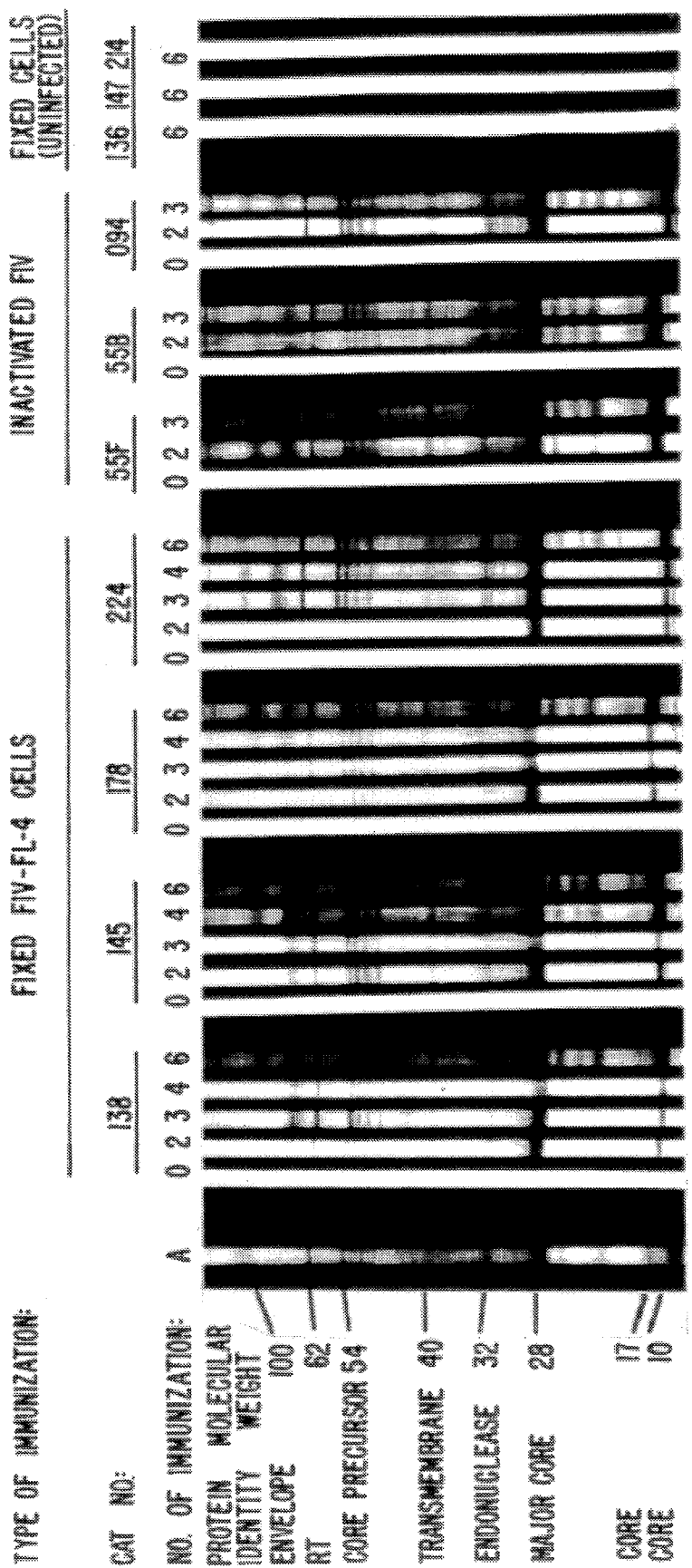

Nine cats in total were vaccinated subcutaneously (SC) with $1\times10^7$ cells mixed with MDP (250 μg) five times at two week intervals and a final boost was given two months later. Five cats received the FIV-FeT1 cells (Group 1A) and four cats received the FIV-FL-4 cells (Group B). Ten control cats were inoculated with the uninfected allogeneic T-cells mixed with adjuvant, or adjuvant alone (Groups 1C and 1D, Table 2). Both fixed cell-virus vaccines induced significant levels of FIV antibodies (1:5,000 to 1:50,000) after the first boost as detected by whole-virus ELISA (FIG. 6A). By immunoblot, all nine vaccinated cats showed antibody to the viral core protein p24 after the first boost and antibody to other viral antigens, including the envelope gp100, after the third or fourth immunization (FIG. 7). Antibody response to the cellular components of the vaccine was weak as determined by immunoblot reactivity to the fixed uninfected cells. FIV-neutralizing antibody titers of 1:800 to 1:1200 were reached after the final immunization; these titers were equal to or slightly higher than the titers observed in unvaccinated cats experimentally infected with FIV (FIG. 8A). No infectious virus was detected in the vaccinated cats prior to challenge. Control cats remained free of antiviral antibodies and of infectious virus during the immunization schedule. The results are summarized in Table 2.

TABLE 2

| | Isolation of FIV from Vaccinated Cats Before and After FIV-challenge | | | | | | |
|---|---|---|---|---|---|---|---|
| GROUP CODE | GROUP 1A | GROUP 1B | GROUP 1C | GROUP 1D | GROUP 2A | GROUP 2B | GROUP 2C |
| CAT # | 135,137,142, 150,209 | 145,224,138, 178 | 136,147,164, 214,227 | 175,215,270, 271,278 | 55B,55F,094 | 55C,55I,177 | 182,55D,55H |
| VACCINE TYPE | FIV-FeT1 Cells | FIV-FL-4 Cells | FeT1 Cells (uninfected) | Placebo | Whole | Whole Virus + FeT1 Cells (uninfected) | Placebo |

TABLE 2-continued

Isolation of FIV from Vaccinated Cats Before and After FIV-challenge

| FIV ISOLATION (Positive Cat#) | | | | | | | |
|---|---|---|---|---|---|---|---|
| From PBL | | | | | | | |
| Pre-challenge | – | – | – | – | – | – | – |
| 2 weeks post-challenge (pc) | – | – | – | – | ND | ND | ND |
| 3 weeks pc | – | – | 147,214,227 | 175,270,278 | – | – | – |
| 5 weeks pc | 209 | 178 | 147,214,227 | 175,270,278 | ND | ND | ND |
| 7 weeks pc | – | 178 | ALL | ALL | – | 551 | ALL |
| 17 weeks pc | – | 178 | ALL | ALL | – | – | ALL |
| 21 weeks pc | – | 138,178 | ALL | ALL | ND | ND | ND |
| 26 weeks pc | – | 138,178 | ALL | ALL | ND | ND | ND |
| From Bone Marrow | | | | | | | |
| 21 weeks pc | – | 138,178 | ALL | ALL | – | – | ALL |
| PCR OF PBL | | | | | | | |
| 21 weeks pc | – | 138,178 | ALL | ALL | – | – | ALL |
| TOTAL # INFECTED | 1/5 | 2/4 | 5/5 | 5/5 | 0/3 | 1/3 | 3/3 |
| TOTAL # CHALLENGED | (Transient) | (Persistent) | (Persistent) | (Persistent) | | (Transient) | |

– Indicates negative result.
Number indicates positive result from a specific cat with corresponding identification number.
ALL indicates that all cats in the specific group are positive.
ND indicates not done.

Two weeks after the final immunization, all of the cats were challenged intraperitoneally (IP) with 10 animal infectious doses ($AID_{100}$) of the homologous FIV strain. Starting at seven weeks post challenge (pc) all ten control cats seroconverterd, antibody titers gradually increased, and virus was persistently isolated from their peripheral blood lymphocytes (PBLs) (Table 2). By contrast, a steady fall in antibodies occurred and virus could not be isolated from the PBLs of six of the nine vaccinated cats for ≧21 weeks pc. These six cats were also free of detectable virus at 17 weeks pc as measured by bone marrow culture and polymerase chain reaction (PCR) analysis of PBLs and bone marrow cells. They therefore seemed to be solidly protected without evidence of latent proviral DNA. In one of the vaccinated cats (#209), virus was recovered from PBLs only one occasion, at 5 weeks pc. after which it was no longer detectable in either the PBLs (by virus isolation and PCR) or the bone marrow cells (by virus isolation). Antibody levels decreased steadily in this animal. Therefore, this animal may also be protected. Virus was recovered persistently after 5 weeks pc from the PBLs of one vaccinated cat (#178) and after 21 weeks pc from another vaccinated cat (#138). The PBLs of both animals were PCR positive at 21 weeks pc at which time infectious virus was isolated from their bone marrow. These two persistently infected cats showed a sudden rise in antibodies by ELISA at the time virus was recovered, and the antibodies remained high thereafter (FIG. 6A). Also, by immunoblot, both core and envelope antibodies persisted longer in these cats than in the protected cats. These late breakthroughs of infectious virus in cats that had previously appeared protected indicate that only time can confirm the absence of latent virus in the protected vaccinates. At 27 weeks pc, the seven vaccine protected cats showed FIV specific cell mediated response (CMR) as measured by positive lymphocyte proliferation and IL-2 induction assays (FIGS. 9A and 9B) as well as a positive response to non-specific mitogens (data not shown). By contrast, the two persistently infected vaccinates and all infected control cats showed a lack of cellular response to FIV while the non-specific mitogen response remained intact. Since these cats were not tested for CMR before challenge we do not know if they were genetically poor responders and therefore vulnerable to infection or whether these defects in CMI were the result of infection. These findings suggest that the fixed cell-virus vaccine had induced T-cell immunity in the apparently protected cats. The duration of memory T-cell and the possible vaccine induction of cytotoxic T-lymphocytes remain to be determined.

Vaccination with Inactivated Whole Virus and Post Vaccination Challenge

The cell-free whole virus vaccine was prepared from FIV-FL-4. Virus released from this cell line in high titer ($5\times10^8$ cells produced 1 mg viral protein per litter) was pelleted, filtered (0.45 μm), inactivated with paraformaldehyde, and given with a combination of Freund's complete and incomplete adjuvants. Analysis of the cell-free pelleted FIV preparation from the whole-virus vaccine by immunoblot using serum from an FIV immunized cat showed that this vaccine contained all of the viral antigens, although a lesser amount of env glycoproteins than was present in the fixed infected cell vaccine, and also a trace amount of cellular antigens (data not shown). Six cats were immunized SC with 200 μg viral proteins given every two weeks×4. Three control cats received either adjuvant or diluent alone. Significant levels of FIV antibodies (1:20,000 to 1:35,000) detected by whole-virus ELISA were induced after the first boost (FIG. 6B). By immunoblot, core p24 antibodies developed in all cats after the first boost and envelope gp100 antibodies developed in five of six cats after the third immunization (FIG. 7). Just prior to challenge, neutralizing antibody titers to FIV of 1:100 to 1:600 were present in all vaccinates (FIG. 8B). All cats were free of infectious virus prior to challenge.

Two weeks after the final immunization, cats were challenged IP with 10 ID of FIV. PBL cultures became virus and PCR positive by seven weeks pc from the three controls (Table 2), whereas five of six vaccinated cats remained uninfected up to 14 weeks. The PBLs of one vaccinated cat (#55I) were transiently infected at 7 weeks pc but were negative by virus isolation and PCR at 17 weeks pc. After challenge, gradual decreases in antibody titers were observed in all immunized and protected cats including the single transiently infected cat. These findings show that effective protection against FIV challenge infection can also be achieved with an inactivated whole-virus vaccine.

Both the fixed cell-virus and whole-virus vaccines appeared to give roughly equal protection against challenge infection. However, the whole-virus vaccine was less immunogenic and required about 20-fold more cells to produce the amount of viral protein required to raise antibody titers to the levels approximating those observed with the fixed cell-virus vaccine. Nevertheless, the neutralization titers were still several fold less with the cell-free virus vaccine. This difference can probably be attributed to the difference in adjuvant used and/or to the greater amount and integrity of viral antigens presented on infected cells as compared to cell-free virus (Yamamoto et al. (in the press) Intervirol., and Hosie and Jarrett (1990) AIDS 4:215–220). The cell-virus vaccine may also have elicited an allogenic effect from the inclusion of other cellular antigens. However, a mixture of uninfected allogeneic (FeT1) cells and inactivated whole virus (Table 1, Group 2B) did not enhance the ELISA and neutralizing antibodies to FIV as compared to whole virus alone. This indicates that the expression of viral antigens on the infected cell apparently provides the most effective immunogenicity.

The specific viral proteins and specific immune responses that account for the vaccine protection observed are as yet uncertain. Viral envelope appears an essential determinant because, in another trial, cats immunized with an FIV Iscom vaccine that was deficient in envelope antigen failed to make gp120 antibody and were not protected against challenge infection with 20 $ID_{50}$ of homologous virus. The vaccines of the present invention probably achieved a minimal threshold of protection because, using a similar fixed cell-virus vaccine we were previously unable to protect against a higher challenge dose ($5\times10^3$ ID) of virus (data not shown). Although neutralizing antibody would seem a logical mechanism, other means of vaccine protection, such as antibody dependent complement lysis or cellular cytotoxicity (ADCC) against cell-free virus or infected cells, may also contribute.

Although the foregoing invention has been described in some detail by way of illustration and example for purposes of clarity of understanding, it will be obvious that certain changes and modifications may be practiced within the scope of the appended claims.

What is claimed is:

1. A vaccine comprising an immunogen capable of eliciting an immune response protective against infection by feline immunodeficiency virus (FIV) when administered in an effective amount to a susceptible host, wherein the immunogen provides immunological protection against FIV.

2. A vaccine as in claim 1, further comprising an adjuvant.

3. A method for protecting a cat against FIV infection, said method comprising administering to said cat an effective dose of a vaccine comprising an immunogen capable of eliciting an immune response protective against infection by FIV.

* * * * *

UNITED STATES PATENT AND TRADEMARK OFFICE
CERTIFICATE OF CORRECTION

PATENT NO. : 5,510,106

DATED : April 23, 1996

INVENTOR(S) : Janet K. Yamamoto and Niels D. Pedersen

It is certified that error appears in the above-indentified patent and that said Letters Patent is hereby corrected as shown below:

On the title page, insert item:

--[*] Notice: The term of this patent shall not extend
beyond the expiration date of Pat. No. 5,275,813.--

Signed and Sealed this

Seventh Day of October, 1997

Attest:

BRUCE LEHMAN

Attesting Officer

Commissioner of Patents and Trademarks